(12) United States Patent
Thomae et al.

(10) Patent No.: US 7,371,523 B1
(45) Date of Patent: May 13, 2008

(54) PHENYLETHANOLAMINE-N-METHYLTRANSFERASE SEQUENCE VARIANTS

(75) Inventors: Bianca A. Thomae, Bay Village, OH (US); Eric D. Wieben, Rochester, MN (US); Richard M. Weinshilboum, Rochester, MN (US); Yuan Ji, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 357 days.

(21) Appl. No.: 10/755,018

(22) Filed: Jan. 9, 2004

Related U.S. Application Data

(60) Provisional application No. 60/438,930, filed on Jan. 9, 2003.

(51) Int. Cl.
*C12Q 1/68* (2006.01)
*C12Q 1/48* (2006.01)
*C12N 9/14* (2006.01)
*C07H 21/02* (2006.01)
*C07H 21/04* (2006.01)

(52) U.S. Cl. .................... 435/6; 435/195; 435/15; 536/23.2; 536/24.1

(58) Field of Classification Search .................... 435/6, 435/195, 15; 536/23.2, 23.1
See application file for complete search history.

(56) References Cited

U.S. PATENT DOCUMENTS

| | | | |
|---|---|---|---|
| 5,451,683 A | 9/1995 | Barrett et al. | |
| 5,733,729 A | 3/1998 | Lipshutz et al. | |
| 5,770,722 A | 6/1998 | Lockhart et al. | |
| 6,660,476 B2 * | 12/2003 | Comings et al. | 435/6 |
| 2001/0053519 A1 * | 12/2001 | Fodor et al. | 435/6 |

FOREIGN PATENT DOCUMENTS

| | | |
|---|---|---|
| WO | WO98/20019 | 5/1998 |
| WO | WO99/57318 | 11/1999 |

OTHER PUBLICATIONS

GeneBank Accession No. AC079199.9.*
Aravinda chakravarti SNP Report submission: rs5638.*
Chin, "On the preparation and utilization of isolated and purified oligonucleotides," University of North Carolina, Mar. 9, 2002 (on CD due to large volume of pages).
GenBank Accession No. J03727 dated Jan. 8, 1995.
GenBank Accession No. X52730 dated Apr. 24, 1993.
Böttner et al., "Increased Body Fat Mass and Suppression of Circulating Leptin Levels in Response to Hypersecretion of Epinephrine in Phenylethanolamine-N-Methyltransferase (PNMT)-Overexpressing Mice," *Endocrinology*, 2000, 141(11):4239-4246.
Caine et al., "Recombinant human phenylethanolamine N-methyltransferase: overproduction in *Escherichia coli*, purification, and characterization," *Protein Expr. Purif.*, 1996, 8(2):159-166.
Chadwick et al., "Heterozygote and Mutation Detection by Direct Automated Fluorescent DNA Sequencing Using a Mutant *Taq* DNA Polymerase," *BioTechniques*, 1996, 20:676-683.
Cibelli et al., "Cloned Transgenic Calves Produced from Nonquiescent Fetal Fibroblasts," *Science*, 1998, 280:1256-1258.
Cleland, "Computer Programmes For Processing Enzyme Kinetic Data," *Nature*, 1963, 198:463-365.
Cote et al., "Generation of human monoclonal antibodies reactive with cellular antigens," *Proc. Natl. Acad. Sci. USA*, 1983, 80:2026-2030.
Cole et al., "The EBV-Hybridoma Technique and its Application to Human Lung Cancer," *Monoclonal Antibodies and Cancer Therapy*, 1985, Alan R. Liss, Inc., pp. 77-96.
Excoffier and Slatkin, "Maximum-Likelihood Estimation of Molecular Haplotype Frequencies in a Diploid Population," *Mol. Biol. Evol.*, 1995, 12(5):921-927.
Gearhart et al., "Phenylethanolamine N-methyltransferase has beta-carboline 2N-methyltransferase activity: hypothetical relevance to Parkinson's disease," *Neurochem. Int.*, 2002, 40(7):611-620.
Gordon et al., "*Consed*: A Graphical Tool for Sequence Finishing," *Genome Res.*, 1998, 8:195-202.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nature Genet.*, 1996, 14:441-447.
Halushka et al., "Patterns of single-nucleotide polymorphisms in candidate genes for blood-pressure homeostasis," *Nature Genet.*, 1999, 22:239-247.
Hartl and Clark, "Chromosomes and Heredity," *Principles of Population Genetics*, 3rd Edition, 1997, Sinauer Associates, Inc., Sunderland, MA, pp. 96-106.
Hedrick, *Genetics of Populations*, 2nd Edition, 2000, Jones and Bartlett, Sudbury, MA, pp. 396-405.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorgan. Med. Chem.*, 1996, 4(1):5-23.
Köhler and Milstein, "Continuous cultures of fused cells secreting antibody of predefined specificity," *Nature*, 1975, 256(5512):495-497.
Kozbor and Roder, "The production of monoclonal antibodies from human lymphocytes," *Immunology Today*, 1983, 4:72-79.

(Continued)

*Primary Examiner*—Nashaat T. Nashed
*Assistant Examiner*—Kagnew Gebreyesus
(74) *Attorney, Agent, or Firm*—Fish & Richardson P.C.

(57) ABSTRACT

Isolated PNMT nucleic acid molecules that include a nucleotide sequence variant and nucleotides flanking the sequence variant are described, as well as PNMT allozymes. Methods for determining if a subject is predisposed to multiple sclerosis, early-onset Alzheimer's disease, or Parkinson's disease also are described.

10 Claims, 10 Drawing Sheets

OTHER PUBLICATIONS

Lewis, "PCR's Competitors Are Alive and Well and Moving Rapidly Towards Commercialization," *Genetic Engineering News*, 1992, 12(9):1-3.

Long et al., "An E-M Algorithm and Testing Strategy for Multiple-Locus Haplotypes," *Am. J. Hum. Genet.*, 1995, 56:799-810.

Mann et al., "Association between the phnylethanolamine N-methyltransferase gene and multiple sclerosis," *J. Neuroimmunol.*, 2002, 124(1-2):101-105.

Mann et al., "Phenylethanolamine N-methyltransferase (*PNMT*) Gene and Early-Onset Alzheimer Disease," *Am. J. Med. Genet.*, 2001, 105(4):312-316.

Molinoff et al., "A Sensitive Enzymatic Assay for Dopamine-β-Hydroxylase," *J. Phamacol. Exp. Ther.*, 1971, 178(3):425-431.

Myakishev et al., "High-Throughput SNP Genotyping by Allele-Specific PCR with Universal Energy-Transfer-Labeled Primers," *Genome Research*, 2001, 11(1):163-169.

Nickerson et al., "PolyPhred: automating the detection and genotyping of single nucleotide substitutions using fluorescence-based resequencing," *Nucl. Acids Res.*, 1997, 25(14):2745-2751.

Prince et al., "Robust and Accurate Single Nucleotide Polymorphism Genotyping by Dynamic Allele-Specific Hybridization (DASH): Design Criteria and Assay Validation," *Genome Res.*, 2001, 11(1):152-162.

Schafer and Hawkins, "DNA variation and the future of human genetics," *Nat. Biotechnol.*, 1998, 16:33-39.

Shastry, "Gene disruption in mice: Models of development and disease," *Mol. Cell. Biochem.*, 1998, 181:163-179.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug Dev.*, 1997, 7:187-195.

Tai et al., "Glucocorticoid Responsiveness of the Rat Phenylethanolamine N-methyltransferase Gene," *Mol. Pharmacol.*, 2002, 61(6):1385-1392.

Terwilliger and Ott, "Linkage Disequilibrium between Alleles at Marker Loci," *Handbook of Human Genetic Linkage*, 1994, The Johns Hopkins University Press, Baltimore, pp. 188-193.

Underhill et al., "Detection of Numerous Y Chromosome Biallelic Polymorphisms by Denaturing High-Performance Liquid Chromatography," *Genome Res.*, 1997, 7:996-1005.

Wakayama et al., "Full-term development of mice from enuleated oocytes injected with cumulus cell nuclei," *Nature*, 1998, 394(6691):369-374.

Warthan et al., "Phenylethanolamine N-methyl transferase expression in mouse thymus and spleen," *Brain Behav. Immun.*, 2002, 16(4):493-499.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Wilmut et al., "Viable offspring derived from fetal and adult mammalian cells," *Nature*, 1997, 385(6619):810-813.

Wong et al., "Human GM-CSF: Molecular Cloning of the Complementary DNA and Purification of the Natural and Recombinant Proteins," *Science*, 1985, 228:810-815.

Begun et al., "Crystallization of PNMT, the adrenaline-synthesizing enzyme, is critically dependent on a high protein concentration," *Acta Crystallogr. D. Biol. Crystallogr.*, 2002, 58(Pt 2):314-315.

Burke et al., "Evidence for decreased transport of PNMT protein in advanced Alzheimer's disease," *J. Am. Geriatr. Soc.*, 1990, 38(12):1275-1282.

Comings, "Clinical and molecular genetics of ADHD and Tourette syndrome. Two related polygenic disorders," *Ann. N Y Acad. Sci.* 2001, 931:50-83.

Dubb et al., "Studies with a PNMT inhibitor," *Clin. Pharmacol. Ther.*, 1979, 25(6):837-844.

Grunewald et al., "Phenylethanolamine N-methyltransferase kinetics: bovine versus recombinant human enzyme," *Bioorg. Med. Chem. Lett.*, 2001, 11(12):1579-1582.

Hemmick et al., "Regulation of PNMT gene promoter constructs transfected into the TE 671 human medulloblastoma cell line," *Neurosci. Lett.*, 1995, 201(1):77-80.

Hoehe et al., "Genetic linkage of the human gene for phenylethanolamine N-methyltransferase (PNMT), the adrenaline-synthesizing enzyme, to DNA markers on chromosome 17q21-q22," *Hum. Mol. Genet.*, 1992, 1(3):175-178.

Johannson et al., "Phenylethanolamine N-methyltransferase-like immunoreactivity in psoriasis. An immunohistochemical study on catecholamine synthesizing enzymes and neuropeptides of the skin," *Acta Derm. Venerol.*, 1987, 67(1):1-7.

Kaneda et al., "Molecular cloning of cDNA and chromosomal assignment of the gene for human phenylethanolamine N-methyltransferase, the enzyme for epinephrine biosynthesis," *J. Biol. Chem.*, 1988, 263(16):7672-7677.

Kaneda et al., "Identification of the essential cysteinyl residue located in the active site of human phenylethanolamine N-methyltransferase," *Biochem. Biophys. Res. Commun.*, 1998, 249(2):405-409.

Lew et al., "Localization and characterization of phenylethanolamine N-methyl transferase in the brain of various mammalian species," *Brain Res.*, 1977, 119(1):199-210.

Martin et al., "Getting the adrenaline going: crystal structure of the adrenaline-synthesizing enzyme PNMT," *Structure (Camb)*, 2001, 9(10):977-985.

Reid et al., "Radioenzymatic determination of phenylpropanolamine in plasma," *Anal. Biochem.*, 1987, 165(2):275-86.

Saito et al., "Identification of 197 genetic variations in six human methyltranferase genes in the Japanese population," *J. Hum. Genet.*, 2001, 6(9):529-537.

Wu and Comings, "Two single nucleotide polymorphisms in the promoter region of the human phenylethanolamine N-methyltransferase PNMT gene," *Psychiatr. Genet.*, 1999, 9(4):187-188.

Yoo-Hun et al., "Cloning and analysis of the pseudogene for human epinephrine synthesizing enzyme, phenylethanolamine N-methyltransferase (PNMT)," *Int. J. Biochem.*, 1990, 22(8):921-924.

* cited by examiner

Figure 1 – page 1

```
    CTGGCACTGGGTGGTAACCAGCAAGCCAGCTGGCATCCGCATCCAGGGTTTGTTTCAATG
  1 ---------+---------+---------+---------+---------+---------+  60
    GACCGTGACCCACCATTGGTCGTTCGGTCGACCGTAGGCGTAGGTCCCAAACAAAGTTAC

ATGTCTCGTGGAGAATATGGAGGGGCTGGTGCCAGGACTGTCCTTGGCTTTGCCTCGGGG
 61 ---------+---------+---------+---------+---------+---------+ 120
    TACAGAGCACCTCTTATACCTCCCCGACCACGGTCCTGACAGGAACCGAAACGGAGCCCC

TGTGAACGGGGTCAGTGACCTCTAAAACTAACCTGCCTCTCAGTTCTGAATCCAGACAGA
121 ---------+---------+---------+---------+---------+---------+ 180
    ACACTTGCCCCAGTCACTGGAGATTTTGATTGGACGGAGAGTCAAGACTTAGGTCTGTCT

ATCAATCCTCAGCTGTGTCTCGCTCCACACCCCTGCCCTGGAAGCCAGGGAAGGTTGGA
181 ---------+---------+---------+---------+---------+---------+ 240
    TAGTTAGGAGTCGACACAGAGCGAGGTGTGGGGACGGGACCTTCGGTCCCTTCCAACCT

GGTGCTAGGGGGTCAGGCTCCCCTCTGTGACCCCTGCAGCTGTTGTGGTGACTCATGTCC
241 ---------+---------+---------+---------+---------+---------+ 300
    CCACGATCCCCCAGTCCGAGGGGAGACACTGGGGACGTCGACAACACCACTGAGTACAGG

CAACCTAGCTGCCTCTCCCAAGGAGACTTTCCCCTGGGACAAGGGGGAGGGAATGGCATG
301 ---------+---------+---------+---------+---------+---------+ 360
    GTTGGATCGACGGAGAGGGTTCCTCTGAAAGGGGACCCTGTTCCCCCTCCCTTACCGTAC

GAGGAGGCCCACATCAAGCGGGGCCAGGAACCCACGGTGGCAGGAGCTGGGCTGGTGACC
361 ---------+---------+---------+---------+---------+---------+ 420
    CTCCTCCGGGTGTAGTTCGCCCCGGTCCTTGGGTGCCACCGTCCTCGACCCGACCACTGG

TACCCAGGGCAGAAGGGCCCGGGACTCATCCAGAGGGGAAGGAAGGGGTCTTCAGGAAGA
421 ---------+---------+---------+---------+---------+---------+ 480
    ATGGGTCCCGTCTTCCCGGGCCCTGAGTAGGTCTCCCCTTCCTTCCCCAGAAGTCCTTCT

CCACGGAGATGCCACAGGCAGAATTGGCTTCCCATCTGGGAGATAGGTGGGGAGACCCTG
481 ---------+---------+---------+---------+---------+---------+ 540
    GGTGCCTCTACGGTGTCCGTCTTAACCGAAGGGTAGACCCTCTATCCACCCCTCTGGGAC

GCATTTTGACAGCCAGAACCTGGGGTGCTGAGCAGAATCTTCATGCCTGGCCTGGCCGCC
541 ---------+---------+---------+---------+---------+---------+ 600
    CGTAAAACTGTCGGTCTTGGACCCCACGACTCGTCTTAGAAGTACGGACCGGACCGGCGG

TTCGGAGGGAAGCTGGAGGGTTGGGTGCGAGAGGAGTGGGGTCAGAGCCCCTACATCCGC
601 ---------+---------+---------+---------+---------+---------+ 660
    AAGCCTCCCTTCGACCTCCCAACCCACGCTCTCCTCACCCCAGTCTCGGGGATGTAGGCG

AGGACCCCAAATCGGCTGGGCCCAAGGCCCGGACTGCGCTCCCCGGTGGCCCCGGCGGC
661 ---------+---------+---------+---------+---------+---------+ 720
    TCCTGGGGTTTAGCCGACCCGGGGTTCCGGGCCTGACGCGAGGGGCCACCGGGCCGCCG

CCTCCGCGAATGCGTCCTGCCCCTCCCCTGCCCAAGCCCTCTGCCCTCACCCGGGTCCGG
721 ---------+---------+---------+---------+---------+---------+ 780
    GGAGGCGCTTACGCAGGACGGGGAGGGGACGGGTTCGGGAGACGGGAGTGGGCCCAGGCC
```

Figure 1 – page 2

```
        CGCCGCCCCCGAAGTGGCGGGAACAACCCGAACCCGAACCTTCTGTCCTCGGGAGCCCCC
  781   ---------+---------+---------+---------+---------+---------+  840
        GCGGCGGGGGCTTCACCGCCCTTGTTGGGCTTGGGCTTGGAAGACAGGAGCCCTCGGGGG

AGATAAGCGGCTGGGAACCCGCGGGGCCCGCAGGGGAGGCCCGGCTGTTCCGCCCGCTAA
  841   ---------+---------+---------+---------+---------+---------+  900
        TCTATTCGCCGACCCTTGGGCGCCCCGGGCGTCCCCTCCGGGCCGACAAGGCGGGCGATT

GTGCATTAGCACAGCTCACCTCCCCTATCGCGCCTGCCATCGGACGGGCAGTGCCGCGCC
  901   ---------+---------+---------+---------+---------+---------+  960
        CACGTAATCGTGTCGAGTGGAGGGGATAGCGCGGACGGTAGCCTGCCCGTCACGGCGCGG

CTGCTCTGGGGCCCCCGGAGCGACCACAGCGGAGGCCGGAACGGACTGTCCTTTCTGGGG
  961   ---------+---------+---------+---------+---------+---------+ 1020
        GACGAGACCCCGGGGGCCTCGCTGGTGTCGCCTCCGGCCTTGCCTGACAGGAAAGACCCC

CGGGGTGGGGAGGGGGTGTCGCTGGAGGGCCCGGTGGCATAGCAACGGACGAGAGAGGCC
 1021   ---------+---------+---------+---------+---------+---------+ 1080
        GCCCCACCCCTCCCCCACAGCGACCTCCCGGGCCACCGTATCGTTGCCTGCTCTCTCCGG

TGGAGGAGGGGCGGGGAGGGCGAGTTGTGTGGCAGTTCTAAGGGAAGGGTGGGTGCTGGG
 1081   ---------+---------+---------+---------+---------+---------+ 1140
        ACCTCCTCCCCGCCCCTCCCCCTCAACACACCGTCAAGATTCCCTTCCCACCCACGACCC

ACGGGTGTCCGGGAGGGAGGGGAGCCTGGCGGGGTCTGGGGCCTCGTCGCGGAGGGCGCT
 1141   ---------+---------+---------+---------+---------+---------+ 1200
        TGCCCACAGGCCCTCCCTCCCCTCGGACCGCCCCAGACCCCGGAGCAGCGCCTCCCGCGA

GCGAGGGGGAAACTGGGGAAAGGGCCTAATTCCCCAGTCTCCACCTCGAATCAGGAAAGA
 1201   ---------+---------+---------+---------+---------+---------+ 1260
        CGCTCCCCCTTTGACCCCTTTCCCGGATTAAGGGGTCAGAGGTGGAGCTTAGTCCTTTCT

GAAGGGGCGGGCTGCTGGGCAAAAGAGGTGAATGGCTGCGGGGGCTGGAGAAGAGAGAT
 1261   ---------+---------+---------+---------+---------+---------+ 1320
        CTTCCCCGCCCGACGACCCGTTTTCTCCACTTACCGACGCCCCCCGACCTCTTCTCTCTA

GGGAGGGGCCGGCCGGCGGGGTGAGGGGGTCTAAAGATTGTGGGGGTGAGGAACTGAGG
 1321   ---------+---------+---------+---------+---------+---------+ 1380
        CCCTCCCCGGCCGGCCGCCCCACTCCCCCAGATTTCTAACACCCCCACTCCTTGACTCC

GTGGGGGGCGCCCAGAGGCGGGACTCGGGGCGGGGCAGGCGAGGCGGAGGGCGAGGGCTG
 1381   ---------+---------+---------+---------+---------+---------+ 1440
        CACCCCCGCGGGTCTCCGCCCTGAGCCCCGCCCCGTCCGCTCCGCCTCCCGCTCCCGAC

CGGGAGCAAGTACGGAGCCGGGCGTGTGGGGACGATTGCCGCTGCAGCCGCCGCCCCAC
 1441   ---------+---------+---------+---------+---------+---------+ 1500
        GCCCTCGTTCATGCCTCGGCCCCCACACCCCTGCTAACGGCGACGTCGGCGGCGGGGTG

TCACCTCCGGTGTGTCTGCAGCCCGGACACTAAGGGAGATGGATGAATGGGTGGGGAGGA
 1501   ---------+---------+---------+---------+---------+---------+ 1560
        AGTGGAGGCCACACAGACGTCGGGCCTGTGATTCCCTCTACCTACTTACCCACCCCTCCT
```

Figure 1 – page 3

```
     TGCGGCGCACATGGCCCCGGGCGGCTCGGCGGTCAGCTGCCGCCCCCACAGCGGACCGGT
1561 ---------+---------+---------+---------+---------+---------+ 1620
     ACGCCGCGTGTACCGGGGCCCGCCGAGCCGCCAGTCGACGGCGGGGGTGTCGCCTGGCCA

CGGGGCGGGGGTCGGGCGGTAGAAAAAAGGGCCGCGAGGCGAGCGGGGCACTGGGCGGAC
1621 ---------+---------+---------+---------+---------+---------+ 1680
     GCCCCGCCCCCAGCCCGCCATCTTTTTTCCCGGCGCTCCGCTCGCCCCGTGACCCGCCTG

CGCGGCGGCAGCATGAGCGGCGCAGACCGTAGCCCCAATGCGGGCGCAGCCCCTGACTCG
1681 ---------+---------+---------+---------+---------+---------+ 1740
     GCGCCGCCGTCGTACTCGCCGCGTCTGGCATCGGGGTTACGCCCGCGTCGGGGACTGAGC
                 M   S   G   A   D   R   S   P   N   A   G   A   A   P   D   S   -

GCCCCGGGCCAGGCGGCGGTGGCTTCGGCCTACCAGCGCTTCGAGCCGCGCGCCTACCTC
1741 ---------+---------+---------+---------+---------+---------+ 1800
     CGGGGCCCGGTCCGCCGCCACCGAAGCCGGATGGTCGCGAAGCTCGGCGCGCGGATGGAG

A   P   G   Q   A   A   V   A   S   A   Y   Q   R   F   E   P   R   A   Y   L   -

CGCAACAACTACGCGCCCCCTCGCGGGGACCTGTGCAACCCGAACGGCGTCGGGCCGTGG
1801 ---------+---------+---------+---------+---------+---------+ 1860
     GCGTTGTTGATGCGCGGGGGAGCGCCCCTGGACACGTTGGGCTTGCCGCAGCCCGGCACC

R   N   N   Y   A   P   P   R   G   D   L   C   N   P   N   G   V   G   P   W   -

AAGCTGCGCTGCTTGGCGCAGACCTTCGCCACCGGTGAGCGGGGGAAACTGAGGCACGAG
1861 ---------+---------+---------+---------+---------+---------+ 1920
     TTCGACGCGACGAACCGCGTCTGGAAGCGGTGGCCACTCGCCCCCTTTGACTCCGTGCTC

K   L   R   C   L   A   Q   T   F   A   T   G  (SEQ ID NO:3)

GGACAAGAGGTCGTCGGGGAGTGAAAGCAGGCGCAGGGAAATAAAAAGAAGGAAAGGGAG
1921 ---------+---------+---------+---------+---------+---------+ 1980
     CCTGTTCTCCAGCAGCCCCTCACTTTCGTCCGCGTCCCTTTATTTTTCTTCCTTTCCCTC

ACAGACCAGGCGCCTAACAGATGGGGACCAAGAAACAAGAGATAGCTGAGAGGTGCAAAC
1981 ---------+---------+---------+---------+---------+---------+ 2040
     TGTCTGGTCCGCGGATTGTCTACCCCTGGTTCTTTGTTCTCTATCGACTCTCCACGTTTG

AGAAGAGAAAAAGGAGCAACATCCCTTAGGAGAGGGGCAGAGGAGAGAGAGGTGGAGAGA
2041 ---------+---------+---------+---------+---------+---------+ 2100
     TCTTCTCTTTTTCCTCGTTGTAGGGAATCCTCTCCCCGTCTCCTCTCTCTCCACCTCTCT

GGGGGCGGAGAGTGCTCAGAATTGAGAGCTAAGGTGGGGGATGCAGGACAGACTGAGGTG
2101 ---------+---------+---------+---------+---------+---------+ 2160
     CCCCCGCCTCTCACGAGTCTTAACTCTCGATTCCACCCCCTACGTCCTGTCTGACTCCAC

GAGATGCATAGGAGGAAATGGAGGCAGATGTGGGACAGGGGTGAGAAACTCCAGGATTTC
2161 ---------+---------+---------+---------+---------+---------+ 2220
     CTCTACGTATCCTCCTTTACCTCCGTCTACACCCTGTCCCCACTCTTTGAGGTCCTAAAG
```

Figure 1 – page 4

```
          CTCGCTGAGCCTGGCTGGTAGGTATAGTTGTTTTCTTTCTTTTTCTTTATTTTATTTTCA
2221      ---------+---------+---------+---------+---------+---------+ 2280
          GAGCGACTCGGACCGACCATCCATATCAACAAAAGAAAGAAAAAGAAATAAAATAAAAGT

TTTATTTACTTATTTTTATTTTTTATTTGTTTTGAGACGGAGTTTCGCTCTTGTTGCCCA
2281      ---------+---------+---------+---------+---------+---------+ 2340
          AAATAAATGAATAAAAATAAAAAATAAACAAAACTCTGCCTCAAAGCGAGAACAACGGGT

GGCTGGAGTACAATGGCGCCATCTCGGCTCACTGCAACCTCCGCCTCCCCGGGTTCAAGC
2341      ---------+---------+---------+---------+---------+---------+ 2400
          CCGACCTCATGTTACCGCGGTAGAGCCGAGTGACGTTGGAGGCGGAGGGGCCCAAGTTCG

GATTCTCTTGCCTCAGCTTCCCTAGTAGCTGGGATTACAGGCATGCGCCCCCATGCCTGG
2401      ---------+---------+---------+---------+---------+---------+ 2460
          CTAAGAGAACGGAGTCGAAGGGATCATCGACCCTAATGTCCGTACGCGGGGGTACGGACC

CTAATTTATTTGTATTTTTAGTAGAGACGGGACTTCTCCATGTTGGTCAGGCTGGTCTCG
2461      ---------+---------+---------+---------+---------+---------+ 2520
          GATTAAATAAACATAAAAATCATCTCTGCCCTGAAGAGGTACAACCAGTCCGACCAGAGC

AACTCCCAACCTTAGGATCCACCCACCCCGGCCTCCCAAAGTGCTGGGATTACAGGTGTG
2521      ---------+---------+---------+---------+---------+---------+ 2580
          TTGAGGGTTGGAATCCTAGGTGGGTGGGGCCGGAGGGTTTCACGACCCTAATGTCCACAC

AGCCACTGCGCCCGGCCAGTAGGTATAGTCTTCTAGATGTGAAACCTGAGTCTCAGAGCG
2581      ---------+---------+---------+---------+---------+---------+ 2640
          TCGGTGACGCGGGCCGGTCATCCATATCAGAAGATCTACACTTTGGACTCAGAGTCTCGC

GTGAAGTTCCGTTCCGAAGGGCAGCCCATGTTGGAGCTGGGTTCAGTCTAACTCTGGGGC
2641      ---------+---------+---------+---------+---------+---------+ 2700
          CACTTCAAGGGAAGGCTTCCCGTCGGGTACAACCTCGACCCAAGTCAGATTGAGACCCCG

CAATGCTTTTTCCAGATGGAGACACATTTGCAGAGGAGAAGGAAGAACTAGAGAGAGGCA
2701      ---------+---------+---------+---------+---------+---------+ 2760
          GTTACGAAAAAGGTCTACCTCTGTGTAAACGTCTCCTCTTCCTTCTTGATCTCTCTCCGT

GGGAGATGCAGGGGAGGGAAGGGTAAGGAGGCAGGGGCTGCCTGGGCTGGCTGGCACCAG
2761      ---------+---------+---------+---------+---------+---------+ 2820
          CCCTCTACGTCCCCTCCCTTCCCATTCCTCCGTCCCCGACGGACCCGACCGACCGTGGTC

GACCCTCTTCCTCTGCCCTGCCCAGGTGAAGTGTCCGGACGCACCCTCATCGACATTGGT
2821      ---------+---------+---------+---------+---------+---------+ 2880
          CTGGGAGAAGGAGACGGGACGGGTCCACTTCACAGGCCTGCGTGGGAGTAGCTGTAACCA
                                          E  V  S  G  R  T  L  I  D  I  G  -

TCAGGCCCCACCGTGTACCAGCTGCTCAGTGCCTGCAGCCACTTTGAGGACATCACCATG
2881      ---------+---------+---------+---------+---------+---------+ 2940
          AGTCCGGGGTGGCACATGGTCGACGAGTCACGGACGTCGGTGAAACTCCTGTAGTGGTAC
          S  G  P  T  V  Y  Q  L  L  S  A  C  S  H  F  E  D  I  T  M  -
```

Figure 1 – page 5

```
             ACAGATTTCCTGGAGGTCAACCGCCAGGAGCTGGGCGCTGGCTGCAGGAGGAGCCGGGG
    2941     ---------+---------+---------+---------+---------+---------+ 3000
             TGTCTAAAGGACCTCCAGTTGGCGGTCCTCGACCCGCGACCGACGTCCTCCTCGGCCCC

T  D  F  L  E  V  N  R  Q  E  L  G  R  W  L  Q  E  E  P  G   -

GCCTTCAACTGGAGCATGTACAGCCAACATGCCTGCCTCATTGAGGGCAAGGGGTAAGGA
    3001     ---------+---------+---------+---------+---------+---------+ 3060
             CGGAAGTTGACCTCGTACATGTCGGTTGTACGGACGGAGTAACTCCCGTTCCCCATTCCT

A  F  N  W  S  M  Y  S  Q  H  A  C  L  I  E  G  K  G  (SEQ ID NO:4)

CTGGGGGGTGAGGGTTGGGGAGGAGGCTTCCCATAGAGTGGCTGGTTGGGGCAACAGAGG
    3061     ---------+---------+---------+---------+---------+---------+ 3120
             GACCCCCCACTCCCAACCCCTCCTCCGAAGGGTATCTCACCGACCAACCCCGTTGTCTCC

CCTGAGCGTAGAACAGCCTTGAGCCCTGCCTTGTGCCTCCTGCACAGGGAATGCTGGCAG
    3121     ---------+---------+---------+---------+---------+---------+ 3180
             GGACTCGCATCTTGTCGGAACTCGGGACGGAACACGGAGGACGTGTCCCTTACGACCGTC

E  C  W  Q    -

GATAAGGAGCGCCAGCTGCGAGCCAGGGTGAAACGGGTCCTGCCCATCGACGTGCACCAG
    3181     ---------+---------+---------+---------+---------+---------+ 3240
             CTATTCCTCGCGGTCGACGCTCGGTCCCACTTTGCCCAGGACGGGTAGCTGCACGTGGTC

D  K  E  R  Q  L  R  A  R  V  K  R  V  L  P  I  D  V  H  Q   -

CCCCAGCCCCTGGGTGCTGGGAGCCCAGCTCCCCTGCCTGCTGACGCCCTGGTCTCTGCC
    3241     ---------+---------+---------+---------+---------+---------+ 3300
             GGGGTCGGGGACCCACGACCCTCGGGTCGAGGGGACGGACGACTGCGGGACCAGAGACGG

P  Q  P  L  G  A  G  S  P  A  P  L  P  A  D  A  L  V  S  A   -

TTCTGCTTGGAGGCTGTGAGCCCAGATCTTGCCAGCTTTCAGCGGGCCCTGGACCACATC
    3301     ---------+---------+---------+---------+---------+---------+ 3360
             AAGACGAACCTCCGACACTCGGGTCTAGAACGGTCGAAAGTCGCCCGGGACCTGGTGTAG

F  C  L  E  A  V  S  P  D  L  A  S  F  Q  R  A  L  D  H  I   -

ACCACGCTGCTGAGGCCTGGGGGGCACCTCCTCCTCATCGGGGCCCTGGAGGAGTCGTGG
    3361     ---------+---------+---------+---------+---------+---------+ 3420
             TGGTGCGACGACTCCGGACCCCCCGTGGAGGAGGAGTAGCCCCGGGACCTCCTCAGCACC

T  T  L  L  R  P  G  G  H  L  L  L  I  G  A  L  E  E  S  W   -

TACCTGGCTGGGGAGGCCAGGCTGACGGTGGTGCCAGTGTCTGAGGAGGAGGTGAGGGAG
    3421     ---------+---------+---------+---------+---------+---------+ 3480
             ATGGACCGACCCCTCCGGTCCGACTGCCACCACGGTCACAGACTCCTCCTCCACTCCCTC

Y  L  A  G  E  A  R  L  T  V  V  P  V  S  E  E  E  V  R  E   -
```

Figure 1 – page 6

```
       GCCCTGGTGCGTAGTGGCTACAAGGTCCGGGACCTCCGCACCTATATCATGCCTGCCCAC
3481   ---------+---------+---------+---------+---------+---------+ 3540
       CGGGACCACGCATCACCGATGTTCCAGGCCCTGGAGGCGTGGATATAGTACGGACGGGTG

A  L  V  R  S  G  Y  K  V  R  D  L  R  T  Y  I  M  P  A  H  -

CTTCAGACAGGCGTAGATGATGTCAAGGGCGTCTTCTTCGCCTGGGCTCAGAAGGTTGGG
3541   ---------+---------+---------+---------+---------+---------+ 3600
       GAAGTCTGTCCGCATCTACTACAGTTCCCGCAGAAGAAGCGGACCCGAGTCTTCCAACCC

L  Q  T  G  V  D  D  V  K  G  V  F  F  A  W  A  Q  K  V  G  -

CTGTGAGGGCTGTACCTGGTGCCCTGTGGCCCCCACCCACCTGGATTCCCTGTTCTTTGA
3601   ---------+---------+---------+---------+---------+---------+ 3660
       GACACTCCCGACATGGACCACGGGACACCGGGGGTGGGTGGACCTAAGGGACAAGAAACT

L  *   (SEQ ID NO:5)

AGTGGCACCTAATAAAGAAATAATACCCTGCCGCTGCGGTCAGTGCTGTGTGTGGCTCTC
3661   ---------+---------+---------+---------+---------+---------+ 3720
       TCACCGTGGATTATTTCTTTATTATGGGACGGCGACGCCAGTCACGACACACACCGAGAG

CTGGGAAGCAGCAAGGGCCCAGAGATCTGAGTGTCCGGGTAGGGGAGACATTCACCCTAG
3721   ---------+---------+---------+---------+---------+---------+ 3780
       GACCCTTCGTCGTTCCCGGGTCTCTAGACTCACAGGCCCATCCCCTCTGTAAGTGGGATC

GCTTTTTTTCCAGAAGCTT   (SEQ ID NO:1)
3781   ---------+--------- 3799
       CGAAAAAAAGGTCTTCGAA   (SEQ ID NO:2)
```

Figure 2A – page 1

```
     GGCAGCATGAGCGGCGCAGACCGTAGCCCCAATGCGGGCGCAGCCCCTGACTCGGCCCCG
  1  ---------+---------+---------+---------+---------+---------+  60
     CCGTCGTACTCGCCGCGTCTGGCATCGGGGTTACGCCCGCGTCGGGGACTGAGCCGGGGC

M   S   G   A   D   R   S   P   N   A   G   A   A   P   D   S   A   P   -

GGCCAGGCGGCGGTGGCTTCGGCCTACCAGCGCTTCGAGCCGCGCGCCTACCTCCGCAAC
 61  ---------+---------+---------+---------+---------+---------+  120
     CCGGTCCGCCGCCACCGAAGCCGGATGGTCGCGAAGCTCGGCGCGCGGATGGAGGCGTTG

G   Q   A   A   V   A   S   A   Y   Q   R   F   E   P   R   A   Y   L   R   N   -

AACTACGCGCCCCTCGCGGGGACCTGTGCAACCCGAACGGCGTCGGGCCGTGGAAGCTG
121  ---------+---------+---------+---------+---------+---------+  180
     TTGATGCGCGGGGGAGCGCCCCTGGACACGTTGGGCTTGCCGCAGCCCGGCACCTTCGAC

N   Y   A   P   P   R   G   D   L   C   N   P   N   G   V   P   W   K   L   -

CGCTGCTTGGCGCAGACCTTCGCCACCGGTGAAGTGTCCGGACGCACCCTCATCGACATT
181  ---------+---------+---------+---------+---------+---------+  240
     GCGACGAACCGCGTCTGGAAGCGGTGGCCACTTCACAGGCCTGCGTGGGAGTAGCTGTAA

R   C   L   A   Q   T   F   A   T   G   E   V   S   G   R   T   L   I   D   I   -

GGTTCAGGCCCCACCGTGTACCAGCTGCTCAGTGCCTGCAGCCACTTTGAGGACATCACC
241  ---------+---------+---------+---------+---------+---------+  300
     CCAAGTCCGGGGTGGCACATGGTCGACGAGTCACGGACGTCGGTGAAACTCCTGTAGTGG

G   S   G   P   T   V   Y   Q   L   L   S   A   C   S   H   F   E   D   I   T   -

ATGACAGATTTCCTGGAGGTCAACCGCCAGGAGCTGGGGCGCTGGCTGCAGGAGGAGCCG
301  ---------+---------+---------+---------+---------+---------+  360
     TACTGTCTAAAGGACCTCCAGTTGGCGGTCCTCGACCCCGCGACCGACGTCCTCCTCGGC

M   T   D   F   L   E   V   N   R   Q   E   L   G   R   W   L   Q   E   E   P   -

GGGGCCTTCAACTGGAGCATGTACAGCCAACATGCCTGCCTCATTGAGGGCAAGGGGGAA
361  ---------+---------+---------+---------+---------+---------+  420
     CCCCGGAAGTTGACCTCGTACATGTCGGTTGTACGGACGGAGTAACTCCCGTTCCCCCTT

G   A   F   N   W   S   M   Y   S   Q   H   A   C   L   I   E   G   K   G   E   -

TGCTGGCAGGATAAGGAGCGCCAGCTGCGAGCCAGGGTGAAACGGGTCCTGCCCATCGAC
421  ---------+---------+---------+---------+---------+---------+  480
     ACGACCGTCCTATTCCTCGCGGTCGACGCTCGGTCCCACTTTGCCCAGGACGGGTAGCTG

C   W   Q   D   K   E   R   Q   L   R   A   R   V   K   R   V   L   P   I   D   -

GTGCACCAGCCCCAGCCCCTGGGTGCTGGGAGCCCAGCTCCCCTGCCTGCTGACGCCCTG
481  ---------+---------+---------+---------+---------+---------+  540
     CACGTGGTCGGGGTCGGGGACCCACGACCCTCGGGTCGAGGGGACGGACGACTGCGGGAC

V   H   Q   P   Q   P   L   G   A   G   S   P   A   P   L   P   A   D   A   L   -
```

Figure 2A – page 2

```
      GTCTCTGCCTTCTGCTTGGAGGCTGTGAGCCCAGATCTTGCCAGCTTTCAGCGGGCCCTG
541   ---------+---------+---------+---------+---------+---------+  600
      CAGAGACGGAAGACGAACCTCCGACACTCGGGTCTAGAACGGTCGAAAGTCGCCCGGGAC

V  S  A  F  C  L  E  A  V  S  P  D  L  A  S  F  Q  R  A  L   -

GACCACATCACCACGCTGCTGAGGCCTGGGGGGCACCTCCTCCTCATCGGGGCCCTGGAG
601   ---------+---------+---------+---------+---------+---------+  660
      CTGGTGTAGTGGTGCGACGACTCCGGACCCCCGTGGAGGAGGAGTAGCCCCGGGACCTC

D  H  I  T  T  L  L  R  P  G  G  H  L  L  L  I  G  A  L  E   -

GAGTCGTGGTACCTGGCTGGGGAGGCCAGGCTGACGGTGGTGCCAGTGTCTGAGGAGGAG
661   ---------+---------+---------+---------+---------+---------+  720
      CTCAGCACCATGGACCGACCCCTCCGGTCCGACTGCCACCACGGTCACAGACTCCTCCTC

E  S  W  Y  L  A  G  E  A  R  L  T  V  V  P  V  S  E  E  E   -

GTGAGGGAGGCCCTGGTGCGTAGTGGCTACAAGGTCCGGGACCTCCGCACCTATATCATG
721   ---------+---------+---------+---------+---------+---------+  780
      CACTCCCTCCGGGACCACGCATCACCGATGTTCCAGGCCCTGGAGGCGTGGATATAGTAC

V  R  E  A  L  V  R  S  G  Y  K  V  R  D  L  R  T  Y  I  M   -

CCTGCCCACCTTCAGACAGGCGTAGATGATGTCAAGGGCGTCTTCTTCGCCTGGGCTCAG
781   ---------+---------+---------+---------+---------+---------+  840
      GGACGGGTGGAAGTCTGTCCGCATCTACTACAGTTCCCGCAGAAGAAGCGGACCCGAGTC

P  A  H  L  Q  T  G  V  D  D  V  K  G  V  F  F  A  W  A  Q   -

AAGGTTGGGCTGTGAGGGCTGTACCTGGTGCCCTGTGGCCCCCACCCACCTGGATTCCCT
841   ---------+---------+---------+---------+---------+---------+  900
      TTCCAACCCGACACTCCCGACATGGACCACGGGACACCGGGGGTGGGTGGACCTAAGGGA

K  V  G  L  *    (SEQ ID NO:8)

GTTCTTTGAAGTGGCACCTAATAAAGAAATAATACC   (SEQ ID NO:6)
901   ---------+---------+---------+------  936
      CAAGAAACTTCACCGTGGATTATTTCTTTATTATGG   (SEQ ID NO:7)
```

Figure 2B

```
    MSGADRSPNAGAAPDSAPGQAAVASAYQRFEPRAYLRNNYAPPRGDLCNPNGVGPWKLRC
  1 ---------+---------+---------+---------+---------+---------+  60

LAQTFATGEVSGRTLIDIGSGPTVYQLLSACSHFEDITMTDFLEVNRQELGRWLQEEPGA
 61 ---------+---------+---------+---------+---------+---------+ 120

FNWSMYSQHACLIEGKGECWQDKERQLRARVKRVLPIDVHQPQPLGAGSPAPLPADALVS
121 ---------+---------+---------+---------+---------+---------+ 180

AFCLEAVSPDLASFQRALDHITTLLRPGGHLLLIGALEESWYLAGEARLTVVPVSEEEVR
181 ---------+---------+---------+---------+---------+---------+ 240

EALVRSGYKVRDLRTYIMPAHLQTGVDDVKGVFFAWAQKVGL  (SEQ ID NO:8)
241 ---------+---------+---------+---------+--- 282
```

PHENYLETHANOLAMINE-N-METHYLTRANSFERASE SEQUENCE VARIANTS

CROSS-REFERENCE TO RELATED APPLICATIONS

This application claims priority from U.S. Provisional Application Ser. No. 60/438,930, filed Jan. 9, 2003.

STATEMENT AS TO FEDERALLY SPONSORED RESEARCH

This invention was made with government support under grant Nos. GM28157 and GM61388, awarded by the National Institutes of Health. The government has certain rights in the invention.

TECHNICAL FIELD

The invention relates to PNMT nucleic acid and amino acid sequence variants.

BACKGROUND

Catecholamine neurotransmitters (dopamine, norepinephrine, and epinephrine) are synthesized in catecholaminergic neurons from tyrosine, via dopa, dopamine, and norepinephrine, to epinephrine. Four enzymes are involved in the biosynthesis of epinephrine: (1) tyrosine 3-mono-oxygenase (tyrosine hydroxylase, TH); (2) aromatic L-amino acid decarboxylase (AADC, or DOPA decarboxylase, DDC); (3) dopamine beta-mono-oxygenase (dopamine beta-hydroxylase, DBH); and (4) phenylethanolamine N-methyltransferase (PNMT, EC 2.1.1.28). PNMT is a cytosolic enzyme that catalyzes the synthesis of epinephrine from norepinephrine. PNMT is expressed in chromaffin cells of the adrenal medulla, medulla oblongata, hypothalamus, and sensory nuclei of the vagus nerve. The gene encoding PNMT maps to a region of the human genome that is associated with multiple sclerosis, and polymorphisms within the promoter of the PNMT gene are associated with multiple sclerosis. Polymorphisms in the promoter of the PNMT gene also have been implicated in early-onset Alzheimer's disease.

SUMMARY

The invention is based on the discovery of sequence variants that occur in both coding and non-coding regions of PNMT nucleic acids. Certain PNMT nucleotide sequence variants encode PNMT enzymes that are associated with individual differences in enzymatic activity. Other PNMT sequence variants in non-coding regions of the PNMT nucleic acid may alter regulation of transcription and/or splicing of the PNMT nucleic acid. Discovery of these sequence variants allows individual differences in the methylation of drugs and other xenobiotics in humans to be assessed such that particular treatment regimens can be tailored to an individual based on the presence or absence of one or more sequence variants. Identification of PNMT sequence variants also allows predisposition to multiple sclerosis, early-onset Alzheimer's disease, Parkinson's disease, psoriasis, attention deficit hyperactivity disorder (ADHD), Tourette's syndrome, and hypertension to be assessed in individuals.

In one aspect, the invention features an isolated nucleic acid molecule containing a PNMT nucleic acid sequence, wherein the nucleic acid molecule is at least ten nucleotides in length, and wherein the PNMT nucleic acid sequence comprises a nucleotide sequence variant. The nucleotide sequence variant can be at a position selected from the group consisting of: (a) position 32, 159, 298, 340, or 462 of SEQ ID NO:6; (b) position 1, 360, 616, or 757 relative to the guanine in the splice donor site of intron 1 within SEQ ID NO:1; (c) position 940 or 941 relative to the adenine of the PNMT translation initiation codon within SEQ ID NO:1, and (d) position −591, −392, −390, −229, or −184 relative to the adenine in the PNMT translation initiation codon within SEQ ID NO:1.

The nucleotide sequence variant can be a nucleotide substitution or a nucleotide insertion. The nucleotide sequence variant can be a thymine substitution for cytosine at position 940 relative to the adenine of the PNMT translation initiation codon or an adenine substitution for guanine at position 941 relative to the adenine of the PNMT translation initiation codon. The nucleotide sequence variant can be a thymine substitution for guanine at position 1 relative to the guanine in the splice donor site of intron 1, a cytosine substitution for thymine at position 360 relative to the guanine in the splice donor site of intron 1, an adenine substitution for guanine at position 616 relative to the guanine in the splice donor site of intron 1, or an adenine substitution for cytosine at position 757 relative to the guanine in the splice donor site of intron 1.

The nucleotide sequence variant can be a thymine substitution for guanine at position −591 relative to the adenine in the PNMT translation initiation codon within SEQ ID NO:1, a cytosine substitution for guanine at position −392 relative to the adenine in the PNMT translation initiation codon within SEQ ID NO:1, an adenine substitution for guanine at position −390 relative to the adenine in the PNMT translation initiation codon within SEQ ID NO:1, an adenine substitution for guanine at position −229 relative to the adenine in the PNMT translation initiation codon within SEQ ID NO:1, or an adenine substitution for guanine at position −184 relative to the adenine in the PNMT translation initiation codon within SEQ ID NO:1.

The nucleotide sequence variant at position 32 of SEQ ID NO:6 can be a guanine substitution for adenine. The nucleotide sequence variant at position 159 of SEQ ID NO:6 can be a thymine substitution for cytosine. The nucleotide sequence variant at position 298 of SEQ ID NO:6 can be a guanine substitution for adenine. The nucleotide sequence variant at position 340 of SEQ ID NO:6 can be a thymine substitution for cytosine. The nucleotide sequence variant at position 462 of SEQ ID NO:6 can be a guanine substitution for adenine.

In another aspect, the invention features an isolated nucleic acid encoding a PNMT polypeptide, wherein the polypeptide contains a PNMT amino acid sequence variant relative to the amino acid sequence of SEQ ID NO:8. The amino acid sequence variant can be at a residue selected from the group consisting of 9, 98, and 112 (e.g., a serine at residue 9, an alanine at residue 98, or a cysteine at residue 112).

In another aspect, the invention features an isolated PNMT polypeptide, wherein the polypeptide contains a PNMT amino acid sequence variant relative to the amino acid sequence of SEQ ID NO:8. The amino acid sequence variant can be at a residue selected from the group consisting of 9, 98, and 112 (e.g., a serine at residue 9, an alanine at residue 98, or a cysteine at residue 112). Activity of the polypeptide can be altered relative to a wild type PNMT polypeptide.

The invention also features an isolated nucleic acid molecule containing a PNMT nucleic acid sequence, wherein the nucleic acid molecule is at least ten nucleotides in length, wherein the PNMT nucleic acid sequence has at least 99% sequence identity to a region of SEQ ID NO:1 or SEQ ID NO:6. Nucleotide 940 or 941 relative to the adenine of the PNMT translation initiation codon can be a thymine or an adenine, respectively, or nucleotides 32, 159, 298, 340, and/or 462 of SEQ ID NO:6 can be a guanine, thymine, guanine, thymine, and guanine, respectively. The region can be selected from the group consisting of nucleotides 1 of 100 of SEQ ID NO:6, nucleotides 100 to 200 of SEQ ID NO:6, nucleotides 250 to 350 of SEQ ID NO:6, nucleotides 300 to 375 of SEQ ID NO:6, and nucleotides 420 to 500 of SEQ ID NO:6.

In yet another aspect, the invention features an article of manufacture including a substrate, wherein the substrate includes a population of isolated PNMT nucleic acid molecules, and wherein the nucleic acid molecules include a PNMT nucleotide sequence variant. The substrate can include a plurality of discrete regions, wherein each region includes a different population of isolated PNMT nucleic acid molecules, and wherein each population of molecules includes a different PNMT nucleotide sequence variant.

The invention also features a method for determining if a subject (e.g., a mammal such as a human) is predisposed to multiple sclerosis or early-onset Alzheimer's disease. The method can include obtaining a biological sample from a subject, and detecting the presence or absence of a PNMT nucleotide sequence variant in the sample, wherein predisposition to multiple sclerosis or early-onset Alzheimer's disease is determined based on the presence or absence of a variant. The method can further include detecting the presence or absence of a plurality of PNMT nucleotide sequence variants in the sample to obtain a variant profile of the subject, and wherein predisposition to multiple sclerosis or early-onset Alzheimer's disease is determined based on the variant profile.

In another aspect, the invention features a method for assisting a medical or research professional. The method includes obtaining a biological sample from a subject (e.g., a mammal such as a human), and detecting the presence or absence of a plurality of PNMT nucleotide sequence variants in the sample to obtain a variant profile of the subject. The method can further include communicating the profile to the medical or research professional.

The invention also features an isolated nucleic acid molecule including a PNMT nucleic acid sequence, wherein the nucleic acid molecule is at least ten nucleotides in length, and wherein the PNMT nucleic acid sequence includes at least two nucleotide sequence variants. The variants can be within any combination of coding sequences, intron sequences, 5' untranslated sequences, or 3' untranslated sequences. For example, the variants can be selected from the group consisting of a variant at position 32, 159, 298, 340, or 462 of SEQ ID NO:6, a variant at positions 940 or 941 relative to the adenine in the PNMT translation initiation codon within SEQ ID NO:1, a variant at position 1, 360, 616, or 757 relative to the guanine in the splice donor site of intron 1 within SEQ ID NO:1, and a variant at position −591, −392, −390, −229, and −184 relative to the adenine in the PNMT translation initiation codon within SEQ ID NO:1.

The invention also features a method for determining the methyltransferase status of an individual. The method can include determining whether the subject contains a variant PNMT nucleic acid.

In another aspect, the invention features a method for predicting the therapeutic efficacy of a compound in a subject, wherein metabolism of the compound includes methylation. The method can include: a) determining the methyltransferase status of the subject; and b) correlating the methyltransferase status with the ability of the subject to metabolize the compound, wherein the compound is predicted to be therapeutically effective if the methyltransferase status is enhanced in the subject, and wherein the compound is predicted not to be therapeutically effective if the methyltransferase status is reduced in the subject. Determination of the methyltransferase status can include determining whether the subject contains a variant PNMT nucleic acid (e.g., a variant PNMT nucleic acid having a non-synonymous single nucleotide polymorphism). Determination of the methyltransferase status can include measuring methyltransferase activity (e.g., PNMT activity) in a biological sample from the subject.

In yet another aspect, the invention features a method for predicting the therapeutic efficacy of a compound in a subject, wherein metabolism of the compound includes methylation. The method can include: a) estimating the level of methyltransferase activity in the subject; and b) correlating the level of methyltransferase activity with the ability of the subject to metabolize the compound, wherein the compound is predicted to be therapeutically effective if the level of methyltransferase activity is increased in the subject, and wherein the compound is predicted not to be therapeutically effective if the level of methyltransferase activity is reduced in the subject. The methyltransferase can be PNMT. The methyltransferase activity can be estimated in vitro in a biological sample from the subject. The level of methyltransferase activity in the subject can be estimated by determining whether the subject contains a variant PNMT nucleic acid (e.g., a variant PNMT nucleic acid having a non-synonymous single nucleotide polymorphism).

In another aspect, the invention features a method for estimating the dose of a compound for administration to a subject, wherein metabolism of the compound comprises methylation. The method can include determining the level of methyltransferase activity in a biological sample from the subject, wherein the dose is estimated to be higher if the level of methyltransferase activity is increased in the biological sample as compared to a control level of methyltransferase activity, and wherein the dose is estimated to be lower if the level of methyltransferase activity is decreased in the biological sample as compared to the control level of methyltransferase activity. The methyltransferase activity can be PNMT activity. Determination of the level of methyltransferase activity can include determining whether the subject comprises a variant PNMT nucleic acid (e.g., a variant PNMT nucleic acid having a non-synonymous single nucleotide polymorphism).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1 is a depiction of the nucleotide sequence of the reference PNMT (SEQ ID NO:1) and its complement (SEQ ID NO:2), and the amino acid sequence of the reference PNMT (SEQ ID NOs:3, 4, and 5). Exons are depicted in bold type and introns are in regular type. Positions of single nucleotide polymorphisms (SNPs) are boxed, as are the positions of amino acid changes that result from the SNPs. Primers are underlined, and start and stop codons are double-underlined. The TATA box is italicized. The translation initiation codon begins at nucleotide 1693 of SEQ ID NO:1. Exon 1 contains nucleotides 1693 to 1894 of SEQ ID NO:1. Intron 1 contains nucleotides 1895 to 2845 of SEQ ID NO:1. Exon 2 contains nucleotides 2846 to 3053 of SEQ ID NO:1. Intron 2 contains nucleotides 3054 to 3167 of SEQ ID NO:1. Exon 3 contains nucleotides 3168 to 3606 of SEQ ID NO:1.

FIG. 2A is a depiction of a cDNA sequence (SEQ ID NO:6) containing the open reading frame of the reference PNMT (nucleotides 7-855) and the complementary sequence (SEQ ID NO:7) of the cDNA sequence. FIG. 2A also shows the reference amino acid sequence (SEQ ID NO:8) of the encoded PNMT. Positions of SNPs are bolded and underlined, as are the positions of amino acid changes that result from the SNPs. Start and stop codons are double-underlined. FIG. 2B is the amino acid sequence (SEQ ID NO:8) of the reference PNMT. Amino acids that are changed as a result of SNPs are underlined and bolded.

DETAILED DESCRIPTION

Figure 3:
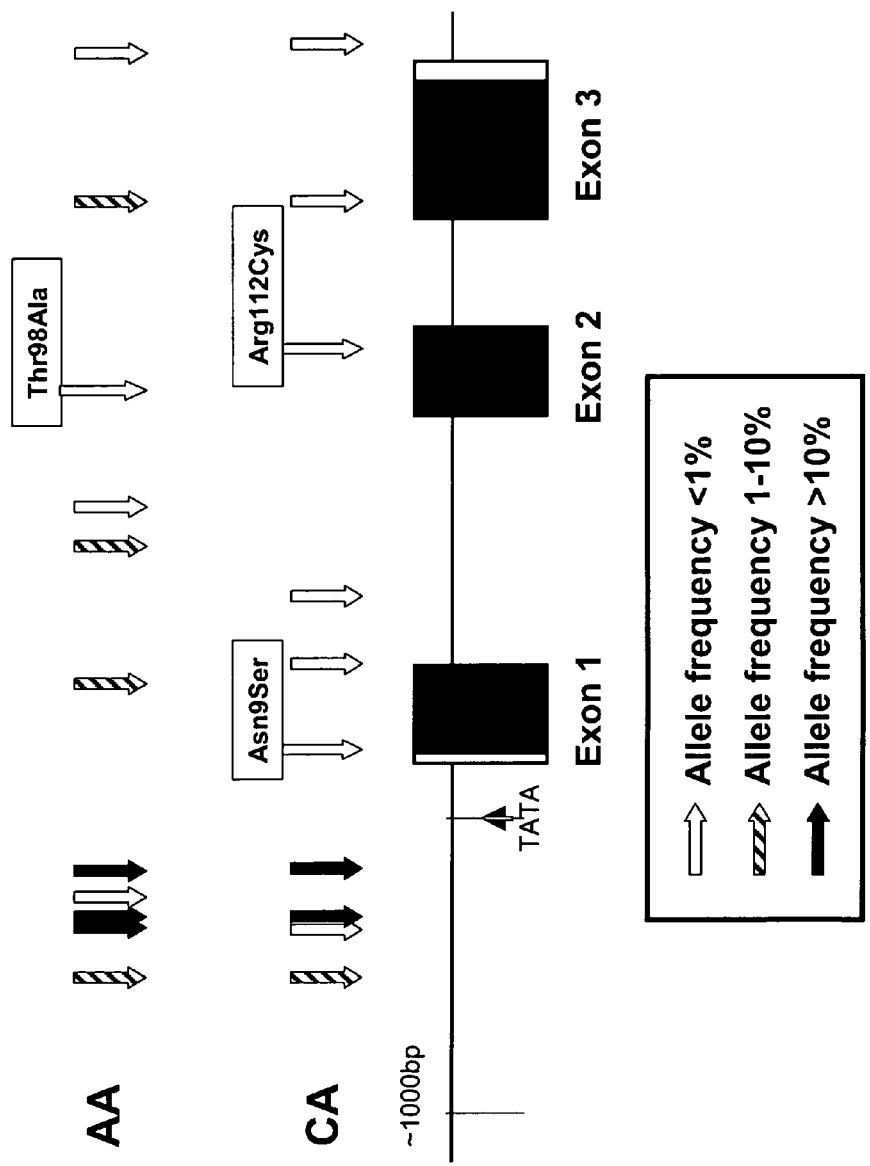
FIG. 3 is a schematic of the locations of polymorphisms within the human PNMT amino acid sequence in Caucasian Americans (CA) and African Americans (AA).

The invention features PNMT nucleotide and amino acid sequence variants. PNMT is an enzyme that N-methylates β-hydroxy phenylethylamines, using S-adenosylmethionine (SAM) as the methyl donor. For example, norepinephrine is N-methylated by PNMT to form epinephrine, which accounts for approximately 80% of the catecholamines in the adrenal medulla. The level of glucocorticoids, which are secreted by the adrenal cortex, controls the rate of synthesis of epinephrine from norepinephrine. Epinephrine has many clinical uses, including relief of respiratory distress due to bronchospasm, rapid relief of hypersensitivity reactions to drugs and other allergens, and prolonging the action of local anesthetics, and restoring cardiac rhythm. Other substrates for PNMT include phenylethanolamine, octopamine, and 9-methylnorharman, a beta-carboline. 2N-methylation of 9-methylnorharman by PNMT may generate 2N-methylated beta-carbolinium cations, which may play a role in idiopathic Parkinson's disease. Genetically-based variations in PNMT activity that lead to altered levels of PNMT or altered PNMT activity may be important in such disorders as multiple sclerosis, early-onset Alzheimer's disease, psoriasis, attention deficit hyperactivity disorder (ADHD), Tourette's syndrome, Parkinson's disease, and hypertension. Thus, detecting methyltransferase nucleic acid and amino acid sequence variants can facilitate the prediction of therapeutic efficacy and toxicity of phenylethylamine drugs (e.g., phenylethanolamine) on an individual basis, as well as indicate predisposition to disorders such as multiple sclerosis and early-onset Alzheimer's disease, for example.

Nucleic Acid Molecules

The invention features isolated nucleic acids that include a PNMT nucleic acid sequence.

The PNMT nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-PNMT proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in a sense or antisense orientation, can be complementary to the PNMT reference sequence (e.g., SEQ ID NO:2 and SEQ ID NO:7), and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in a PNMT reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference PNMT nucleic acid sequence is provided in FIG. 1 (SEQ ID NO:1) and in GenBank (Accession No. X52730). The reference PNMT cDNA including the PNMT ORF is provided in FIG. 2A (SEQ ID NO:6) and the corresponding reference PNMT amino acid sequence is provided in FIG. 2B (SEQ ID NO:8). The mRNA and amino acid reference sequences also are found in GenBank (Accession No. J03727). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences are designated as "–X" relative to the "A" in the translation initiation codon; positions of nucleotide sequence variants in the coding sequence and 3' untranslated sequence are designated as "+X" or "X" relative to the "A" in the translation initiation codon. Nucleotide sequence variants that occur in introns are designated as "+X" or "X" relative to the "G" in the splice donor site (GT) or as "–X" relative to the "G" in the splice acceptor site (AG).

In some embodiments, a PNMT nucleotide sequence variant encodes a PNMT polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-250 residues, or a full-length PNMT polypeptide). PNMT polypeptides may or may not have PNMT catalytic activity, or may have altered activity relative to the reference PNMT polypeptide. Polypeptides that do not have activity or have altered activity can be useful for diagnostic purposes (e.g., for producing antibodies having specific binding affinity for variant PNMT polypeptides).

Corresponding PNMT polypeptides, irrespective of length, that differ in amino acid sequence are herein referred to as allozymes. For example, a PNMT nucleic acid sequence that includes a guanine at position 26 relative to the adenine in the translation initiation codon (i.e., nucleotide 32 of SEQ ID NO:6) encodes a PNMT polypeptide having a serine at amino acid residue 9. This polypeptide (Asn9Ser) would be considered an allozyme with respect to the reference PNMT polypeptide that contains an asparagine at amino acid residue 9. Additional non-limiting examples of PNMT sequence variants that alter amino acid sequence include variants at nucleotides 292 and 334 relative to the adenine in the translation initiation codon (i.e., positions 298 and 340 of SEQ ID NO:6). For example, a PNMT nucleic acid molecule can include a guanine at nucleotide 292 and encode a PNMT polypeptide having an alanine at amino acid residue 98 in place of a threonine residue (Thr98Ala); or a thymine at nucleotide 334 and encode a PNMT polypeptide having a cysteine at amino acid 112 in place of an arginine residue (Arg112Cys).

PNMT allozymes as described above are encoded by a series of PNMT alleles. These alleles represent nucleic acid sequences containing sequence variants, typically multiple sequence variants, within coding and non-coding sequences. Representative examples of single nucleotide variants are described above. Table 2 sets out a series of PNMT alleles that encode PNMT. Some alleles are commonly observed, i.e., have allele frequencies >1%, such as the allele having a guanine at nucleotide 456 in place of an adenine. The relatively large number of alleles and allozymes for PNMT indicates the potential complexity of PNMT pharmacogenetics. Such complexity emphasizes the need for determining single nucleotide variants, (i.e., single nucleotide polymorphisms, SNPs) as well as complete PNMT haplotypes (i.e., the set of alleles on one chromosome or a part of a chromosome) of patients.

Certain PNMT nucleotide sequence variants do not alter the amino acid sequence. Such variants, however, could alter regulation of transcription as well as mRNA stability. PNMT variants can occur in intron sequences, for example, within introns 1 or 2. In particular, the nucleotide sequence variant can include a thymine substitution at nucleotide 1 of intron 1, a cytosine substitution at nucleotide 360 of intron 1, an adenine substitution at nucleotide 616 of intron 1, or an adenine substitution at nucleotide 757 of intron 1.

PNMT nucleotide sequence variants that do not change the amino acid sequence also can be within an exon or in 5' or 3' untranslated sequences. Exon 1 sequence variants can, for example, include a thymine substitution at nucleotide 153 (i.e., nucleotide 1845 of SEQ ID NO:1 or nucleotide 159 of SEQ ID NO:6). Exon 3 sequence variants can include a guanine substitution at nucleotide 456 (i.e., nucleotide 3213 of SEQ ID NO:1 or nucleotide 462 of SEQ ID NO:6). Nucleotide sequence variants in the 5' flanking region can include a thymine substitution at nucleotide –591, a cytosine substitution at nucleotide –392, an adenine substitution at nucleotide –390, an adenine substitution at nucleotide –229, or an adenine substitution at nucleotide –184 relative to the adenine in the translation initiation codon (i.e., nucleotides 1102, 1301, 1303, 1464, or 1509 of SEQ ID NO:1, respectively). Nucleotide sequence variants in the 3' UTR can include a thymine substitution at nucleotide 940 or an adenine substitution at nucleotide 941 (i.e., nucleotides 3693 or 3694 of SEQ ID NO:1, respectively).

In some embodiments, nucleic acid molecules of the invention can have at least 97% (e.g., 97.5%, 98%, 98.5%, 99.0%, 99.5%, 99.6%, 99.7%, 99.8%, 99.9%, or 100%) sequence identity with a region of SEQ ID NO: 1, SEQ ID NO:2, SEQ ID NO:6, or SEQ ID NO:7 that includes one or more variants described herein. The region of SEQ ID NO:1, 2, 6, or 7 is at least ten nucleotides in length (e.g., 10, 15, 20, 50, 60, 70, 75, 100, 150 or more nucleotides in length). For example, a nucleic acid molecule can have at least 99% identity with nucleotides 1 to 75, 1 to 100, 75 to 150, 100 to 200, 150 to 225, 225 to 300, 250 to 350, 300 to 375, 375 to 425, 420 to 500, 425 to 500, 500 to 575, 575 to 625, 625 to 700, 700 to 775, 775 to 825, 825 to 900, or 875 to 936 of SEQ ID NO:6, where the nucleotide sequence of SEQ ID NO:6 includes one or more of the variants described herein. For example, the nucleotide sequence of SEQ ID NO:6 can have a guanine at nucleotide 32, a thymine at nucleotide 159, a guanine at nucleotide 298, a thymine at nucleotide 340, or a guanine at nucleotide 462, and combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO:1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a PNMT nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis *Genetic Engineering News*, 12(9):1 (1992); Guatelli et al., *Proc. Natl. Acad. Sci. USA*, 87:1874-1878 (1990); and Weiss, *Science*, 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequences depicted in FIG. 1 or 2A can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

PNMT Polypeptides

Isolated PNMT polypeptides of the invention include an amino acid sequence variant relative to the reference PNMT (FIG. 2B, GenBank Accession No. J03727 or AAA60130.1). The term "isolated" with respect to a PNMT polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

PNMT polypeptides of the invention include variants at one or more of amino acid residues 9, 98, and 112. In particular, a serine residue can be substituted at position 9, an alanine residue at position 98, or a cysteine residue at position 112. In some embodiments, activity of PNMT polypeptides is altered relative to the reference PNMT. Certain PNMT allozymes can have reduced activity, while other allozymes can have activity that is comparable to the reference PNMT. Other allozymes can have increased activity relative to the reference PNMT. Activity of PNMT polypeptides can be assessed in vitro. For example, the activity of PNMT polypeptides can be assessed by determining the amount of [$^{14}$C]-N-methyl-phenylethanolamine that is produced by a recombinant methyltransferase (e.g., recombinant PNMT) in the presence of $^{14}$C-SAM and phenylethanolamine (2 mg/mL) or octopamine (0.2 mg/mL), for example.

Other biochemical properties of allozymes, such as apparent $K_m$ values, also can be altered relative to the reference PNMT. Apparent $K_m$ values can be calculated, for example, by using the method of Wilkinson with a computer program written by Cleland. Wilkinson, *Biochem. J.*, 80:324-332 (1961); and Cleland, *Nature*, 198:463-365 (1963).

Isolated polypeptides of the invention can be obtained, for example, by extraction from a natural source (e.g., brain tissue), chemical synthesis, or by recombinant production in a host cell. To recombinantly produce PNMT polypeptides, a nucleic acid encoding a PNMT nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a PNMT nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine (His$_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express PNMT variant polypeptides. For example, BL-21 cells can be transformed with a pGEX vector containing a PNMT nucleic acid sequence. The transformed bacteria can be grown exponentially and then stimulated with isopropylthiogalactopyranoside (IPTG) prior to harvesting. In general, the PNMT-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed PNMT polypeptide can be released from the GST moiety.

In eukaryotic host cells, a number of viral-based expression systems can be utilized to express PNMT variant polypeptides. A nucleic acid encoding a polypeptide of the invention can be cloned into, for example, a baculoviral vector such as pBlueBac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Eukaryotic cell lines that stably express PNMT variant polypeptides can be produced using expression vectors with the appropriate control elements and a selectable marker. For example, the eukaryotic expression vector pCR3.1 (Invitrogen, San Diego, Calif.) and p91023(B) (see Wong et al., *Science* (1985) 228:810-815) or modified derivatives thereof are suitable for expression of PNMT variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (Invitrogen) and then transcribed and translated in vitro using wheat germ extract or rabbit reticulocyte lysate.

PNMT variant polypeptides can be purified by known chromatographic methods including ion exchange and gel filtration chromatography. See, for example, Caine et al., *Protein Expr. Purif.* (1996) 8(2):159-166. PNMT polypeptides can be "engineered" to contain a tag sequence describe herein that allows the polypeptide to be purified (e.g., captured onto an affinity matrix). Immunoaffinity chromatography also can be used to purify PNMT polypeptides.

Non-Human Mammals

The invention features non-human mammals that include PNMT nucleic acids of the invention, as well as progeny and cells of such non-human mammals. Non-human mammals include, for example, rodents such as rats, guinea pigs, and mice, and farm animals such as pigs, sheep, goats, horses, and cattle. Non-human mammals of the invention can express a PNMT variant nucleic acid in addition to an endogenous PNMT (e.g., a transgenic non-human that includes a PNMT nucleic acid randomly integrated into the genome of the non-human mammal). Alternatively, an endogenous PNMT nucleic acid can be replaced with a PNMT variant nucleic acid of the invention by homologous recombination. See, Shastry, *Mol. Cell. Biochem.*, (1998) 181(1-2):163-179, for a review of gene targeting technology.

In one embodiment, non-human mammals are produced that lack an endogenous PNMT nucleic acid (i.e., a knockout), and then a PNMT variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous PNMT nucleic acid. That is, cultured ES cells can be transformed with a knockout construct and cells selected in which the PNMT gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning A Laboratory Manual*, second edition, Cold Spring Harbor Press, Plainview; NY, 1989.

To generate a knockout animal, ES cells having at least one inactivated PNMT allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated PNMT allele. If the original ES cell was heterozygous for the inactivated PNMT allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the PNMT gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous PNMT gene and express a PNMT nucleic acid of the invention, and then fused with enucleated oocytes. After activation of the oocytes, the eggs are cultured to the blastocyst stage, and implanted into a recipient. See, Cibelli et al., *Science*, (1998) 280:1256-1258. Adult somatic cells, including, for example, cumulus cells and mammary cells, can be used to produce animals such as mice and sheep, respectively. See, for example, Wakayama et al., *Nature*, (1998) 394(6691):369-374; and Wilmut et al., *Nature*, (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al. 1998, supra.

Non-human mammals of the invention such as mice can be used, for example, to screen toxicity of compounds that are substrates for PNMT, drugs that alter PNMT activity, or for carcinogenesis. For example, PNMT activity or toxicity can be assessed in a first group of such non-human mammals in the presence of a compound, and compared with PNMT activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting PNMT Sequence Variants

PNMT nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33-39), denaturing high performance liquid chromatography (DHPLC, Underhill et al., 1997, *Genome Res.*, 7:996-1005), infrared matrix-assisted laser desorption/ionization (IR-MALDI) mass spectrometry (WO 99/57318), and combinations of such methods.

Genomic DNA generally is used in the analysis of PNMT nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the PNMT gene can be amplified then directly sequenced. Dye primer sequencing can be used to increase the accuracy of detecting heterozygous samples.

Allele specific hybridization also can be used to detect sequence variants, including complete haplotypes of a subject (e.g., a mammal such as a human). See, Stoneking et al., 1991, *Am. J. Hum. Genet.* 48:370-382; and Prince et al., 2001, *Genome Res.*, 11(1):152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For PNMT sequence variants that do not alter a common restriction site, mutagenic primers can be designed that introduce a restriction site when the variant allele is present or when the wild type allele is present. A portion of PNMT nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of PNMT can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, PNMT variants can be detected by antibodies that have specific binding affinity for variant PNMT polypeptides. Variant PNMT polypeptides can be produced in various ways, including recombinantly, as discussed above. Host animals such as rabbits, chickens, mice, guinea pigs, and rats can be immunized by injection of a PNMT variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a PNMT variant polypeptide and standard hybridoma technology. In particular, monoclonal antibodies can be obtained by any technique that provides for the production of antibody molecules by continuous cell lines in culture such as described by Kohler et al., *Nature,* 256:495 (1975), the human B-cell hybridoma technique (Kosbor et al., *Immunology Today,* 4:72 (1983); Cole et al., *Proc. Natl. Acad. Sci USA,* 80:2026 (1983)), and the EBV-hybridoma technique (Cole et al., *Monoclonal Antibodies and Cancer Therapy,* Alan R. Liss, Inc., pp. 77-96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a PNMT variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science,* 246: 1275 (1989). Once produced, antibodies or fragments thereof are tested for recognition of PNMT variant polypeptides by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods

As a result of the present invention, it is possible to determine methyltransferase status of a subject (e.g., a mammal such as a human). "Methyltransferase status" refers to the ability of a subject to transfer a sulfate group to a substrate (e.g., epinephrine). Methyltransferase status of a subject can be determined by, for example, measuring the level of methyltransferase (e.g., PNMT) activity in the subject using, for example, the methods described herein. Alternatively, methyltransferase status can be evaluated by determining whether a methyltransferase nucleic acid sequence (e.g., a PNMT nucleic acid sequence) of a subject contains one or more variants (e.g., one or more variants that are correlated with increased or decreased methyltransferase activity). A variant that results in decreased or increased PNMT activity, for example, can be said to result in "reduced" or "enhanced" methyltransferase status, respectively. In some embodiments, the variant profile of a subject can be used to determine the methyltransferase status of the subject.

"Variant profile" refers to the presence or absence of a plurality (e.g., two or more) of PNMT nucleotide sequence variants or PNMT amino acid sequence variants. For example, a variant profile can include the complete PNMT haplotype of the mammal (e.g., see Table 5) or can include the presence or absence of a set of particular non-synonymous SNPs (e.g., single nucleotide substitutions that alter the amino acid sequence of a PNMT polypeptide). In one embodiment, the variant profile includes detecting the presence or absence of two or more non-synonymous SNPs (e.g., 2, 3, or 4 non-synonymous SNPs) described herein. There may be ethnic-specific pharmacogenetic variation, as certain of the nucleotide and amino acid sequence variants described herein were detected solely in African-American or Caucasian-American subjects. In addition, the variant profile can include detecting the presence or absence of any type of PNMT SNP together with any other PNMT SNP (e.g., a polymorphism pair or a group of polymorphism pairs). Such polymorphism pairs include, without limitation, the pairs described in Table 4. Further, a variant profile can include detecting the presence or absence of any PNMT SNP together with any SNP from other methyltransferase.

Methyltransferase activity of an enzyme such as PNMT can be measured using, for example, in vitro methods such as those described herein. As used herein, the term "reduced methyltransferase status" refers to a decrease (e.g., a 5%, 10%, 15%, 20%, 25%, 30%, 40%, 50%, 60%, 70%, 75%, 80%, 90%, 95%, or 100% decrease) in methyltransferase activity (e.g., PNMT activity) of a subject, as compared to a control level of methyltransferase activity. Similarly, the term "enhanced methyltransferase status" refers to an increase (e.g., a 5%, 10%, 15%, 20%, 25%, 30%, 40%, 50%, 60%, 70%, 75%, 80%, 90%, 95%, 100%, or more than 100% increase) in methyltransferase activity of a subject, as compared to a control level of methyltransferase activity. A control level of methyltransferase activity can be, for example, an average level of methyltransferase activity in a population of individuals. In one embodiment, the population includes individuals that do not contain particular PNMT nucleotide sequence variants or particular PNMT amino acid sequence variants (e.g., particular variants that affect methyltransferase status). Alternatively, a control level of methyltransferase activity can refer to the level of methyltransferase activity in a control subject (e.g., a subject that does not contain a PNMT nucleic acid containing a variant).

In some embodiments, evaluation of methyltransferase status can be used in diagnostic assays to determine whether a particular therapy may be useful in an individual (e.g., whether a subject can metabolize a particular drug). For example, evaluation of methyltransferase status can be useful to predict the therapeutic efficacy and/or potential toxicity of epinephrine therapy in an individual. Norepinephrine may be readily metabolized in a subject with enhanced methyltransferase status, while an individual with reduced methyltransferase status may have reduced capacity to metabolize norepinephrine.

In further embodiments of the invention, methyltransferase status can be linked to predisposition to a particular condition (e.g., multiple sclerosis, early-onset Alzheimer's disease, psoriasis, attention deficit hyperactivity disorder, Tourette's syndrome, Parkinson's disease, or hypertension). Additional risk factors including, for example, family history and other genetic factors can be considered when determining risk. Predisposition to such diseases can be determined based on the presence or absence of a single PNMT sequence variant or based on a variant profile.

Articles of Manufacture

Articles of manufacture of the invention include populations of isolated PNMT nucleic acid molecules or PNMT polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different PNMT nucleic acid or PNMT polypeptide sequence variant. Such articles of manufacture can include two or more sequence variants of PNMT, or can include all of the sequence variants known for PNMT. For example, the article of manufacture can include two or more of the sequence variants identified herein and one or more other PNMT sequence variants, such as nucleic acid variants that occur in the promoter region of the PNMT gene. Furthermore, nucleic acid molecules containing sequence variants for other methyltransferases can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.*, 14:441-447 (1996); and U.S. Pat. Nos. 5,770,722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 Caucasian-American and 60 African-American subjects were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Three PCR reactions were performed with each DNA sample to amplify all PNMT exons and splice junctions. The amplicons were then sequenced using dye-primer sequencing chemistry to facilitate the identification of heterozygous bases (Chadwick et al. *Biotechniques* 20:676-683 (1996)). To make that possible, universal M13 sequencing tags were added to the 5'-ends of each forward and reverse primer. All forward primers contained the M13 forward sequence (5'-TGTAAAACGACG-GCCAGT-3'; SEQ ID NO:9), and all reverse primers contained the M13 reverse sequence (5'-CAGGAAACAGCTATGACC-3'; SEQ ID NO:10). The sequences and locations of each primer within the gene are listed in Table 1. "F" represents forward; "R," reverse; "U," upstream; "D," downstream; "I," intron; "FR," flanking region; and "UTR," untranslated region. The locations of primers within the gene were chosen to avoid repetitive sequence.

Amplifications were performed with AmpliTaq Gold DNA polymerase (Perkin Elmer, Foster City, Calif.) using a "hot start" to help ensure amplification specificity.

Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. To exclude PCR-induced artifacts, independent amplification followed by DNA sequencing was performed for all samples in which a SNP was only observed once among the samples resequenced. DNA sequence chromatograms were analyzed using the PolyPhred 3.0 (Nickerson et al. *Nucl. Acids Res.* 25:2745-2751 (1997)) and Consed 8.0 (Gordon et al. *Genome Res.* 8:195-202 (1998)) programs developed by the University of Washington (Seattle, Wash.). The University of Wisconsin GCG software package, Version 10, was also used to analyze nucleotide sequence. GenBank accession numbers for the PNMT reference sequences were X52730 and J03727.

Recombinant PNMT Expression Constructs and Allozyme Expression: PNMT cDNA sequences for the three non-synonymous cSNPs that were observed during the resequencing experiments were created using the Quick-Change Site-Directed Mutagenesis kit (Stratagene, La Jolla, Calif.), using the wild type PNMT cDNA open reading frame (ORF) in the pUni/V5-His-TOPO (pUni) vector (Invitrogen) as template. Specifically, the full-length wild type ORF (GenBank accession number J03727) was amplified using human brain Marathon-Ready cDNA (Clontech) as template. The resultant PNMT cDNA was subcloned into pUni, a vector that is only 2.3 kilobases in length, so it is well suited for performing "circular PCR" during site-directed mutagenesis. Site-directed mutagenesis was performed using internal primers that contained the variant nucleotide sequences. The PNMT cDNA inserts in pUni were excised and re-ligated into the eukaryotic expression vector p91023(b) (Wong et al. *Science* 228:810-815 (1985)). The sequences of inserts in p91023(b) were confirmed by completely sequencing both strands.

Expression constructs for the wild type and variant PNMT sequences were transfected into COS-1 cells using the TransFast™ reagent (Promega), with a 1:1 charge ratio. pSV-β-Galactosidase (Promega) was co-transfected as an internal control to make it possible to correct for transfection efficiency. The COS-1 cells were harvested after 48 hours and were homogenized with a Polytron homogenizer (Brinkmann Instruments, Westbury, N.Y.) in 25 mM potassium phosphate buffer, pH 7.8 that contained 1 mM dithiothreitol (DTT) and 1 mM EDTA. Cell homogenates were centrifuged at 15,000×g for 15 minutes, and the resultant supernatant preparations were used for enzyme assays and substrate kinetic studies.

expression in COS-1 cells. Since all constructs included an N-terminal His-tag, anti-His monoclonal antibodies (Invitrogen) were used to measure levels of immunoreactive PNMT protein with the ECL detection system (Amersham Pharmacia, Piscataway, N.J.). The quantity of COS-1 cell preparation loaded on the gel for each allozyme was adjusted to achieve equal quantities of β-galactosidase activity, i.e., gel loading was adjusted to correct for transfection

TABLE 1

PCR primers used for resequencing PNMT

| Primer Name | Primer Location | Primer Sequence (5' to 3' direction) | SEQ ID NO |
|---|---|---|---|
| UF(−903)M13 | 5'-FR | TGTAAAACGACGGCCAGTCGAAGTGGCGGGAACAACCCGAA | 11 |
| UR(−505)M13 | 5'-FR | CAGGAAACAGCTATGACCGACGAGGCCCCAGACCCCGCCAGGCT | 12 |
| UF(−591)M13 | 5'-FR | TGTAAAACGACGGCCAGTGAGTTGTGTGGCAGTTCTAAGGGAA | 13 |
| UR(−96)M13 | 5'-FR | CAGGAAACAGCTATGACCGCTGACCGCCGAGCCGCCCGGGGCCATGT | 14 |
| UF(−166)M13 | 5'-FR | TGTAAAACGACGGCCAGTACACTAAGGGAGATGGATGAATGGGT | 15 |
| I1R187m13 | Intron 1 | CAGGAAACAGCTATGACCTCTGCCCCTCTCCTAAGGGATGTT | 16 |
| I1F(−82)M13 | Intron 1 | TGTAAAACGACGGCCAGTAGATGCAGGGGAGGGAAGGGTAA | 17 |
| I1F(146)M13 | Intron 1 | TGTAAAACGACGGCCAGTCAGAAGAGAAAAAGGAGCAACATCCCTTA | 18 |
| I1R(515)M13 | Intron 1 | CAGGAAACAGCTATGACCGGCGCATGCCTGTAATCCCAGCTACTA | 19 |
| I1F(455)M13 | Intron 1 | TGTAAAACGACGGCCAGTCCGGGTTCAAGCGATTCTCTTGCCTCAGCTT | 20 |
| I1R(893)M13 | Intron 1 | CAGGAAACAGCTATGACCGGCAGAGGAAGAGGGTCCTGGT | 21 |
| E3R182M13 | Exon 3 | CAGGAAACAGCTATGACCAAAGCTGGCAAGATCTGGGCTCACAG | 22 |
| E3F133M13 | Exon 3 | TGTAAAACGACGGCCAGTTGGTCTCTGCCTTCTGCTTGGA | 23 |
| DR1032M13 | 3'-FR | CAGGAAACAGCTATGACCAAGCCTAGGGTGAATGTCTCCCCTA | 24 |

Underlined nucleotides indicate M13 tag

PNMT Enzyme Activity: PNMT activity was measured using a method based on that of Molnicoff et al. (1971) *J. Pharmacol. Exp. Ther.* 178(3):425-431. Briefly, 24.22 μM of $^{14}$C-SAM was used as the methyl donor for PNMT-catalyzed methylation of 65.9 μM octopamine. Reactions were performed in 1 M Tris buffer (pH 8.6), with a total volume of 160 μL in 15 mL glass stoppered centrifuge tubes. Cell homogenate preparations of recombinant PNMT allozymes described herein were used for the activity studies without any further purification. "Blank" samples included the same quantity of COS-1 15,000×g supernatant from cells that were transfected with "empty" pCR3.1 expression vector, making it possible to correct for endogenous activity. Reaction mixtures were incubated at 37° C. for 30 minutes, and reactions were stopped with 500 μl Borate Buffer (pH 10). $^{14}$C—N-methyl-octopamine was extracted into toluene containing 20% isoamyl alcohol, and radioactivity of the extracted $^{14}$C—N-methyl-octopamine was measured in a liquid scintillation counter. Activities of the recombinant PNMT allozymes were compared after correction for transfection efficiency by measuring the activity of co-transfected β-galactosidase, using the β-galactosidase Assay System (Promega) as described by the manufacturer.

Estimating Apparent $K_m$ Values: To estimate apparent $K_m$ values of PNMT for the octopamine substrate, a series of octop amine and SAM concentrations were tested with the recombinant allozymes. Blanks for each substrate concentration were included by assaying COS-1 cell cytosol after transfection with empty p91023(b) vector. These data were fitted to a series of kinetic models, and the most appropriate model was selected on the basis of the dispersion of residuals and a determination of whether the F-test showed a significant reduction (P<0.05) in the residual sums of squares. Apparent $K_m$ values were calculated using the method of Wilkinson with a computer program written by Cleland. Wilkinson supra; and Cleland supra.

Western Blot Analysis: Quantitative Western blot analysis was performed with recombinant PNMT allozymes after efficiency. The AMBIS Radioanalytic Imaging System, Quant Probe Version 4.31 (Ambis, Inc., San Diego, Calif.) was used to quantitate immunoreactive protein in each lane, and the data were expressed as a percentage of the intensity of the wild type PNMT band on the gel.

Data Analysis: Statistical comparison of the data was performed by ANOVA using the StatView program, version 4.5 (Abacus Concepts, Inc., Berkeley, Calif.). Linkage analysis was performed after all DNA samples had been genotyped at each of the polymorphic sites observed, using the EH program developed by Terwilliger and Ott, *Handbook of Human Genetic Linkage*, The Johns Hopkins University Press, Baltimore, pp. 188-193 (1994). D' values, a quantitative method for reporting linkage data that is independent of allele frequency (Hartl and Clark *Principles of Population Genetics*, $3^{rd}$ edition, Sinauer Associates, Inc., (Sunderland, Mass.), pp. 96-106 (1997); and Hedrick *Genetics of Populations*, $2^{nd}$ edition, Jones and Bartlett (Sudbury, Mass.), pp. 396-405 (2000)), were calculated. The genotype data also were used to assign inferred haplotypes using a program based on the E-M algorithm (Long et al. *Am. J. Hum. Genet.* 56:799-810 (1995); and Excoffier and Slatkin *Mol. Biol. Evol.* 12:921-927 (1995)). Unambiguous haplotype assignment was possible on the basis of genotype for samples that contained no more than one heterozygous polymorphism.

Example 2

PNMT Polymorphisms

Three separate PCR amplifications were performed for each of the 120 DNA samples studied. All PCR amplicons were sequenced on both strands, making it possible to verify the presence of polymorphisms using data from the complimentary strand. A total of sixteen polymorphisms were observed (Table 2). Polymorphisms in exons, untranslated regions (UTR), and flanking regions (FR) are numbered relative to the adenine in the PNMT translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.8% to 66.7%, with differences between the African-American and Caucasian-American subjects. Eleven polymorphisms were observed in 60 DNA samples from African-American subjects, while ten were found in the 60 samples from Caucasian-American subjects. The overall number of PNMT polymorphisms per kilobase of sequence in the 120 samples studied (5.3 polymorphisms/kilobase; Table 3) was close to that (4.6 polymorphisms/kilobase) observed in similar studies of other human genes (Halushka et al., *Nature Genet.*, 22:239-247 (1999)). Five of the SNPs were within the coding-region (cSNPs), and three of those cSNPs—located in exons 1 and 2—were nonsynonymous and resulted in the amino acid alterations Asn9Ser, Thr98Ala, and Arg112Cys. The Asn9Ser polymorphism had a frequency of 0.8% in Caucasians but was not observed in DNA from African-American subjects. The Thr98Ala polymorphism had a frequency of 0.8% in African Americans, but was not observed in Caucasians. The Arg112Cys polymorphism had a frequency of 0.8% in Caucasians but was not observed in DNA from African-American subjects. To exclude artifacts introduced by PCR-dependent misincorporation, independent amplifications were performed and the amplicons were sequenced in all cases in which a polymorphism was observed only once among the DNA samples studied.

Example 3

Linkage Disequilibrium Analysis and Haplotype Analysis

Linkage disequilibrium analysis was performed after all of the DNA samples had been genotyped at each of the 15 polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate d' values, a method for reporting linkage data that is independent of sample size. Pairwise combinations with a statistically significant linkage disequilibrium are shown in Table 4.

The genotype data also were used for haplotype analysis (Table 5). Seventeen unequivocal haplotypes were identified by these studies. As shown in Table 5, the haplotype analysis accounted for 95.6% and 96.3% of all samples based on these unequivocal haplotypes for DNA samples from African-American and Caucasian-American subjects, respectively. The unequivocal haplotypes included three that were common to both ethnic groups, nine that were ethnic-specific for African-American subjects, and five others that were ethnic-specific for Caucasian-American subjects.

TABLE 2

Human PNMT polymorphisms and frequencies

| Polymorphism Position | Location In Gene | Amino Acid Change | WT Sequence Nucleotide | Variant Sequence Nucleotide | AA | CA |
|---|---|---|---|---|---|---|
| −591 | 5'-FR | | G | T | 0.017 | 0.036 |
| −392 | 5'-FR | | G | C | 0.117 | 0.008 |
| −390 | 5'-FR | | G | A | 0.417 | 0.667 |
| −229 | 5'-FR | | G | A | 0.008 | 0.000 |
| −184 | 5'-FR | | G | A | 0.225 | 0.517 |
| 26 | Exon 1 | Asn9Ser | A | G | 0.000 | 0.008 |
| 153 | Exon 1 | | C | T | 0.017 | 0.000 |
| I1(1) | Intron 1 | | G | T | 0.000 | 0.008 |
| I1(360) | Intron 1 | | T | C | 0.000 | 0.008 |
| I1(616) | Intron 1 | | G | A | 0.033 | 0.000 |
| I1(757) | Intron 1 | | C | A | 0.008 | 0.000 |
| 292 | Exon 2 | Thr98Ala | A | G | 0.008 | 0.000 |
| 334 | Exon 2 | Arg112Cys | C | T | 0.000 | 0.008 |
| 456 | Exon 3 | | A | G | 0.100 | 0.008 |
| 940 | 3'-FR | | C | T | 0.008 | 0.000 |
| 941 | 3'-FR | | G | A | 0.000 | 0.008 |

TABLE 3

PNMT polymorphism frequencies

| SNPs/Kb | Total | African-American | Caucasian |
|---|---|---|---|
| Overall | 5.3 | 3.7 | 3.3 |
| Coding | 6.0 | 3.6 | 3.6 |
| Non-coding | 5.1 | 3.7 | 3.2 |
| UTR | 10.0 | 5.0 | 5.0 |
| Intron | 3.8 | 1.9 | 1.9 |

TABLE 4

Human PNMT linkage disequilibrium analysis

| Polymorphism Pair | | d' Value | |
|---|---|---|---|
| | | AA | CA |
| −390 | −184 | 0.93 | 0.75 |
| −390 | I1(616) | −1 | |
| −390 | 456 | −0.78 | |

TABLE 5

Human PNMT haplotype analysis

| Name | Frequency AA | Frequency CA | Haplotype |
|---|---|---|---|
| *1A | 0.360 | 0.230 | |
| *1B | 0.198 | 0.475 | −390, −184 |
| *1C | 0.142 | 0.161 | −390 |
| *1D | 0.083 | | −392 |
| *1E | 0.064 | | 456 |
| *1F | 0.033 | | I1(616) |
| *1G | 0.025 | | −392, −390 |
| *1H | 0.017 | | 153 |
| *1I | 0.010 | | −390, −184, 456 |
| *1J | 0.008 | | −392, −390, −184 |
| *1K | 0.008 | | −390, I1(757) |
| *1L | | 0.044 | −184 |
| *1M | | 0.027 | −591 |
| *1N | | 0.010 | −591, −390 |
| *2 | 0.008 | | 292 |
| *3 | | 0.008 | 26 |
| *4 | | 0.008 | 334 |

Example 4

Activity, Immunoreactivity, and Substrate Kinetics of PNMT Allozymes

Cell homogenate preparations containing recombinant PNMT allozymes, prepared as described in Example 1, were used to assess catalytic activity. The resulting activities were adjusted to a percentage of the WT PNMT enzyme activity. Asn9Ser exhibited a 7% increase in enzyme activity, and Thr98Ala exhibited a 93% decrease in enzyme activity, while the enzyme activity of Arg112Cys was unchanged from that of the WT PNMT enzyme.

To determine whether the decreased activity of the PNMT variants might be related to quantity of immunoreactive enzyme protein, quantitative Western blot analyses were conducted. These studies revealed that the changes in enzyme activity for the PNMT allozymes were paralleled by similar changes in the levels of immunoreactive protein.

Alterations in amino acid sequence can alter enzyme substrate affinity and/or catalytic efficiency. Substrate kinetic studies were conducted to determine whether the Asn9Ser, Thr98Ala, and Arg112Cys allozymes differed from the WT PNMT protein in these aspects. A series of octopamine and SAM concentrations were used to estimate apparent $K_m$ values for recombinant wild type PNMT and for the three variant allozymes. These studies revealed a significant difference in apparent $K_m$ values between the WT PNMT protein and the Arg112Cys allozyme, for SAM (6.6 µM vs. 15.3 µM, respectively, p=0.04; Table 6). The difference in $K_m$ values for octopamine was nearly significant between the WT PNMT protein and the Arg112Cys allozyme (13.6 µM vs. 23.5 µM, respectively, p=0.06). There was no significant difference in apparent $K_m$ values between the WT protein and the Asn9Ser or Thr98Ala allozymes.

TABLE 6

Recombinant human PNMT biochemical properties

| Poly-morphism | Amino Acid Change | % WT Enzyme activity | % WT Immuno-reactive Protein | Apparent $K_m$ (µM) octopamine | Apparent $K_m$ (µM) SAM |
|---|---|---|---|---|---|
| WT | None | 100 | 100 | 23.5 ± 3.1 | 6.6 ± 1.0 |
| A26G | Asn9Ser | 122.2 ± 7.4 | 109.7 ± 0.9 | 19.2 ± 2.0 | 7.2 ± 0.6 |
| A292G | Thr98Ala | 7.3 ± 1.7 | 16.1 ± 4.1 | 24.5 ± 1.6 | 8.5 ± 0.4 |
| C334T | Arg112Cys | 90.2 ± 4.8 | 97.3 ± 0.2 | 13.6 ± 2.2 | 15.3 ± 2.5 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting essentially of a nucleic acid sequence selected from the group consisting of:
   a) at least fifteen contiguous nucleotides of SEQ ID NO: 6, wherein said sequence includes at least one nucleotide selected from positions 32, 159, 298 and/or 340 of SEQ ID NO: 6, with the proviso that the nucleotide at position 32 is guanine, the nucleotide at position 159 is thymine, the nucleotide at position 298 is guanine and/or the nucleotide at position 340 is thymine; and
   b) the complement of (a).

2. The isolated nucleic acid molecule of claim 1, wherein said nucleotide sequence is at least fifteen contiguous nucleotides of SEQ ID NO:6, wherein said sequence includes nucleotide 159 of SEQ ID NO:6, with the proviso that the nucleotide at position 159 of SEQ ID NO:6 is thymine.

3. The isolated nucleic acid molecule of claim 1, wherein said nucleotide sequence is at least fifteen contiguous nucleotides of SEQ ID NO:6, wherein said sequence includes nucleotide 298 of SEQ ID NO:6, with the proviso that the nucleotide at position 298 of SEQ ID NO:6 is guanine.

4. The isolated nucleic acid molecule of claim 1, wherein said nucleotide sequence is at least fifteen contiguous nucleotides of SEQ ID NO:6, wherein said sequence includes nucleotide 340 of SEQ ID NO:6, with the proviso that the nucleotide at position 340 of SEQ ID NO:6 is thymine.

5. An isolated nucleic acid encoding a PNMT polypeptide, wherein said polypeptide is a variant relative to the amino acid sequence of SEQ ID NO: 8, and wherein said amino acid sequence variation is at a residue selected from the group consisting of 9, 98, and 112.

6. The isolated nucleic acid of claim 5, wherein said amino acid sequence variation is a serine at residue 9, an alanine at residue 98, or a cysteine at residue 112.

7. The isolated nucleic acid molecule of claim 1, wherein said isolated nucleic acid molecule is from 15 to 100 nucleotides in length.

8. The isolated nucleic acid of molecule of claim 1, wherein said isolated nucleic acid molecule is from 20 to 50 nucleotides in length.

9. A vector comprising the nucleic acid molecule of claim 1.

10. The vector of claim 9, wherein said nucleic acid molecule is from 20 to 50 nucleotides in length.

* * * * *

SEQUENCE LISTING

<160> NUMBER OF SEQ ID NOS: 24

<210> SEQ ID NO 1
<211> LENGTH: 3799
<212> TYPE: DNA
<213> ORGANISM: Homo sapien

<400> SEQUENCE: 1

```
ctggcactgg gtggtaacca gcaagccagc tggcatccgc atccagggtt tgtttcaatg      60
atgtctcgtg gagaatatgg aggggctggt gccaggactg tccttggctt tgcctcgggg     120
tgtgaacggg gtcagtgacc tctaaaacta acctgcctct cagttctgaa tccagacaga     180
atcaatcctc agctgtgtct cgctccacac ccctgccct ggaagccagg gaaggttgga      240
ggtgctaggg ggtcaggctc ccctctgtga ccctgcagc tgttgtggtg actcatgtcc      300
caacctagct gcctctccca aggagacttt ccctgggac aaggggagg gaatggcatg       360 gaggaggccc acatcaagcg gggccaggaa cccacggtgg caggagctgg gctggtgacc     420
```

-continued

| | |
|---|---|
| tacccagggc agaagggccc gggactcatc cagaggggaa ggaagggggtc ttcaggaaga | 480 |
| ccacggagat gccacaggca gaattggctt cccatctggg agataggtgg ggagaccctg | 540 |
| gcattttgac agccagaacc tggggtgctg agcagaatct tcatgcctgg cctggccgcc | 600 |
| ttcggaggga agctggaggg ttgggtgcga aggagtgggg gtcagagccc ctacatccgc | 660 |
| aggaccccaa atcggctggg ccccaaggcc cggactgcgc tccccggtgg ccccggcggc | 720 |
| cctccgcgaa tgcgtcctgc ccctcccctg cccaagccct ctgccctcac ccgggtccgg | 780 |
| cgccgccccc gaagtggcgg gaacaacccg aacccgaacc ttctgtcctc gggagccccc | 840 |
| agataagcgg ctgggaaccc gcggggcccg caggggaggc ccggctgttc cgcccgctaa | 900 |
| gtgcattagc acagctcacc tccctatcg cgcctgccat cggacgggca gtgccgcgcc | 960 |
| ctgctctggg gcccccggag cgaccacagc ggaggccgga acggactgtc ctttctgggg | 1020 |
| cggggtgggg aggggtgtc gctggagggc ccggtggcat agcaacggac gagagaggcc | 1080 |
| tggaggaggg gcggggaggg ggagttgtgt ggcagttcta agggaagggt gggtgctggg | 1140 |
| acgggtgtcc gggagggagg ggagcctggc ggggtctggg gcctcgtcgc ggagggcgct | 1200 |
| gcgaggggga aactggggaa agggcctaat tccccagtct ccacctcgaa tcaggaaaga | 1260 |
| gaaggggcgg gctgctgggc aaaagaggtg aatggctgcg gggggctgga agagagagat | 1320 |
| gggagggggcc ggccggcggg ggtgaggggg tctaaagatt gtggggtga ggaactgagg | 1380 |
| gtgggggggcg cccagaggcg ggactcgggg cggggcaggc gaggcggagg gcgagggctg | 1440 |
| cgggagcaag tacggagccg ggggtgtggg ggacgattgc cgctgcagcc gccgccccac | 1500 |
| tcacctccgg tgtgtctgca gcccggacac taagggagat ggatgaatgg gtggggagga | 1560 |
| tgcggcgcac atggccccgg gcggctcggc ggtcagctgc cgcccccaca gcggaccggt | 1620 |
| cggggcgggg gtcgggcggt agaaaaaagg gccgcgaggc gagcggggca ctgggcggac | 1680 |
| cgcggcggca gcatgagcgg cgcagaccgt agccccaatg cgggcgcagc ccctgactcg | 1740 |
| gccccgggcc aggcggcggt ggcttcggcc taccagcgct tcgagccgcg cgcctacctc | 1800 |
| cgcaacaact acgcgccccc tcgcggggac ctgtgcaacc cgaacggcgt cgggccgtgg | 1860 |
| aagctgcgct gcttggcgca gaccttcgcc accggtgagc gggggaaact gaggcacgag | 1920 |
| ggacaagagg tcgtcgggga gtgaaagcag gcgcagggaa ataaaaagaa ggaaagggag | 1980 |
| acagaccagg cgcctaacag atggggacca agaaacaaga gatagctgag aggtgcaaac | 2040 |
| agaagagaaa aaggagcaac atcccttagg agaggggcag aggagagaga ggtgagagaga | 2100 |
| ggggggcggag agtgctcaga attgagagct aaggtggggg atgcaggaca gactgaggtg | 2160 |
| gagatgcata ggaggaaatg gaggcagatg tgggacaggg gtgagaaact ccaggatttc | 2220 |
| ctcgctgagc ctggctggta ggtatagttg ttttctttct ttttctttat tttattttca | 2280 |
| tttatttact tattttattt ttttatttgt tttgagacgg agtttcgctc ttgttgccca | 2340 |
| ggctggagta caatggcgcc atctcggctc actgcaacct ccgcctcccc gggttcaagc | 2400 |
| gattctcttg cctcagcttc cctagtagct gggattacag gcatgcgccc catgcctgg | 2460 |
| ctaatttatt tgtatttta gtagagacgg gacttctcca tgttggtcag gctggtctcg | 2520 |
| aactcccaac cttaggatcc acccaccccg gcctcccaaa gtgctgggat tacaggtgtg | 2580 |
| agccactgcg cccggccagt aggtatagtc ttctagatgt gaaacctgag tctcagagcg | 2640 |
| gtgaagttcc cttccgaagg gcagcccatg ttggagctgg gttcagtcta actctggggc | 2700 |
| caatgctttt tccagatgga gacacatttg cagaggagaa ggaagaacta gagagaggca | 2760 |

-continued

| | |
|---|---|
| gggagatgca ggggagggaa gggtaaggag gcagggctg cctgggctgg ctggcaccag | 2820 |
| gaccctcttc ctctgccctg cccaggtgaa gtgtccggac gcaccctcat cgacattggt | 2880 |
| tcaggcccca ccgtgtacca gctgctcagt gcctgcagcc actttgagga catcaccatg | 2940 |
| acagatttcc tggaggtcaa ccgccaggag ctggggcgct ggctgcagga ggagccgggg | 3000 |
| gccttcaact ggagcatgta cagccaacat gcctgcctca ttgagggcaa ggggtaagga | 3060 |
| ctgggggggtg agggttgggg aggaggcttc ccatagagtg gctggttggg gcaacagagg | 3120 |
| cctgagcgta gaacagcctt gagccctgcc ttgtgcctcc tgcacaggga atgctggcag | 3180 |
| gataaggagc gccagctgcg agccagggtg aaacgggtcc tgcccatcga cgtgcaccag | 3240 |
| ccccagcccc tgggtgctgg gagcccagct cccctgcctg ctgacgccct ggtctctgcc | 3300 |
| ttctgcttgg aggctgtgag cccagatctt gccagctttc agcgggccct ggaccacatc | 3360 |
| accacgctgc tgaggcctgg ggggcacctc ctcctcatcg ggccctgga ggagtcgtgg | 3420 |
| tacctggctg ggggaggccag gctgacggtg gtgccagtgt ctgaggagga ggtgagggag | 3480 |
| gccctggtgc gtagtggcta caaggtccgg gacctccgca cctatatcat gcctgcccac | 3540 |
| cttcagacag gcgtagatga tgtcaagggc gtcttcttcg cctgggctca gaaggttggg | 3600 |
| ctgtgagggc tgtacctggt gccctgtggc ccccacccac ctggattccc tgttctttga | 3660 |
| agtggcacct aataaagaaa taataccctg ccgctgcgg cagtgctgtg tgtggctctc | 3720 |
| ctgggaagca gcaagggccc agagatctga gtgtccgggt aggggagaca ttcaccctag | 3780 |
| gctttttttc cagaagctt | 3799 |

<210> SEQ ID NO 2
<211> LENGTH: 3799
<212> TYPE: DNA
<213> ORGANISM: Homo sapien

<400> SEQUENCE: 2

| | |
|---|---|
| gaccgtgacc caccattggt cgttcggtcg accgtaggcg taggtcccaa acaaagttac | 60 |
| tacagagcac ctcttatacc tccccgacca cggtcctgac aggaaccgaa acggagcccc | 120 |
| acacttgccc cagtcactgg agattttgat tggacggaga gtcaagactt aggtctgtct | 180 |
| tagttaggag tcgacacaga gcgaggtgtg ggggacggga ccttcggtcc cttccaacct | 240 |
| ccacgatccc ccagtccgag gggagacact ggggacgtcg acaacaccac tgagtacagg | 300 |
| gttggatcga cggagagggt tcctctgaaa ggggaccctg ttccccctcc cttaccgtac | 360 |
| ctcctccggg tgtagttcgc cccggtcctt gggtgccacc gtcctcgacc cgaccactgg | 420 |
| atgggtcccg tcttcccggg ccctgagtag gtctcccctt ccttcccag aagtccttct | 480 |
| ggtgcctcta ccggtgtccgt cttaaccgaa gggtagaccc tctatccacc cctctgggac | 540 |
| cgtaaaactg tcggtcttgg accccacgac tcgtcttaga agtacggacc ggaccggcgg | 600 |
| aagcctcct tcgacctccc aacccacgct ctcctcaccc cagtctcggg gatgtaggcg | 660 |
| tcctgggtt tagccgaccc ggggttccgg gcctgacgcg aggggccacc ggggccgccg | 720 |
| ggaggcgctt acgcaggacg gggaggggac gggttcggga cacgggagtg ggcccaggcc | 780 |
| gcggcggggg cttcaccgcc cttgttgggc ttgggcttgg aagacaggag ccctcggggg | 840 |
| tctattcgcc gacccttggg cgccccggc gtcccctccg ggccgacaag gcgggcgatt | 900 |
| cacgtaatcg tgtcgagtgg aggggatagc gcggacggta gcctgcccgt cacggcgcgg | 960 |
| gacgagaccc cgggggcctc gctggtgtcg cctccggcct tgcctgacag gaaagacccc | 1020 |
| gccccacccc tcccccacag cgacctcccg ggccaccgta tcgttgcctg ctctctccgg | 1080 |

```
acctcctccc cgcccctccc cctcaacaca ccgtcaagat tcccttccca cccacgaccc    1140
tgcccacagg ccctccctcc cctcggaccg ccccagaccc cggagcagcg cctcccgcga    1200
cgctccccct ttgaccccctt tcccggatta aggggtcaga ggtggagctt agtcctttct    1260
cttccccgcc cgacgacccg ttttctccac ttaccgacgc cccccgacct cttctctcta    1320
ccctccccgg ccgccgccc ccactcccccc agatttctaa cacccccact ccttgactcc    1380
caccccccgc gggtctccgc cctgagcccc gccccgtccg ctccgcctcc cgctcccgac    1440
gccctcgttc atgcctcggc ccccacaccc cctgctaacg gcgacgtcgg cggcggggtg    1500
agtggaggcc acacagacgt cgggcctgtg attccctcta cctacttacc caccccctcct   1560 acgccgcgtg taccggggcc cgccgagccg ccagtcgacg gcgggggtgt cgcctggcca    1620
gccccgcccc cagcccgcca tcttttttcc cggcgctccg ctcgcccgt gacccgcctg     1680 gcgccgccgt cgtactcgcc gcgtctggca tcggggttac gcccgcgtcg gggactgagc    1740
cggggcccgg tccgccgcca ccgaagccgg atggtcgcga agctcggcgc gcggatggag    1800
gcgttgttga tgcgcggggg agcgcccctg gacacgttgg gcttgccgca gcccggcacc    1860
ttcgacgcga cgaaccgcgt ctggaagcgg tggccactcg ccccctttga ctccgtgctc    1920
cctgttctcc agcagcccct cactttcgtc cgcgtcccctt tattttcctt cctttccctc    1980
tgtctggtcc gcggattgtc taccctggt tctttgttct ctatcgactc tccacgtttg     2040
tcttctcttt ttcctcgttg tagggaatcc tctccccgtc tcctctctct ccacctctct    2100
cccccgcctc tcacgagtct taactctcga ttccaccccc tacgtcctgt ctgactccac    2160
ctctacgtat cctcctttac ctccgtctac accctgtccc cactctttga ggtcctaaag    2220
gagcgactcg gaccgaccat ccatatcaac aaaagaaaga aaagaaata aaataaaagt    2280 aaataaatga ataaaaataa aaataaaaca aaactctgcc tcaaagcgag aacaacgggt    2340
ccgacctcat gttaccgcgg tagagccgag tgacgttgga ggcggagggg cccaagttcg    2400
ctaagagaac ggagtcgaag ggatcatcga ccctaatgtc cgtacgcggg ggtacggacc    2460
gattaaataa acataaaaat catctctgcc ctgaagaggt acaaccagtc cgaccagagc    2520
ttgagggttg gaatcctagg tgggtgggc cggagggttt cacgacccta atgtccacac    2580
tcggtgacgc gggccggtca tccatatcag aagatctaca cttggactc agagtctcgc    2640 cacttcaagg gaaggcttcc cgtcgggtac aacctcgacc caagtcagat tgagaccccg    2700
gttacgaaaa aggtctacct ctgtgtaaac gtctcctctt ccttcttgat ctctctccgt    2760
ccctctacgt ccctctccctt cccattcctc cgtccccgac ggacccgacc gacgtggtc     2820 ctgggagaag gagacgggac gggtccactt cacaggcctg cgtgggagta gctgtaacca    2880
agtccggggt ggcacatggt cgacgagtca cggacgtcgg tgaaactcct gtagtggtac    2940
tgtctaaagg acctccagtt ggcggtcctc gaccccgcga ccgacgtcct cctcggcccc    3000
cggaagttga cctcgtacat gtcggttgta cggacggagt aactcccgtt ccccattcct    3060 gacccccac tcccaacccc tcctccgaag ggtatctcac cgaccaaccc cgttgtctcc    3120
ggactcgcat cttgtcggaa ctcgggacgg aacacggagg acgtgtccct tacgaccgtc    3180
ctattcctcg cggtcgacgc tcggtccac tttgcccagg acgggtagct gcacgtggtc     3240
ggggtcgggg acccacgacc ctcgggtcga ggggacggag gactgcggga ccagagacgg    3300
aagacgaacc tccgacactc gggtctagaa cggtcgaaag tcgcccggga cctggtgtag    3360
tggtgcgacg actccggacc ccccgtggag gaggagtagc cccgggacct cctcagcacc    3420
```

```
atggaccgac ccctccggtc cgactgccac cacggtcaca gactcctcct ccactccctc    3480
cgggaccacg catcaccgat gttccaggcc ctggaggcgt ggatatagta cggacgggtg    3540
gaagtctgtc cgcatctact acagttcccg cagaagaagc ggacccgagt cttccaaccc    3600
gacactcccg acatggacca cgggacaccg ggggtgggtg gacctaaggg acaagaaact    3660
tcaccgtgga ttatttcttt attatgggac ggcgacgcca gtcacgacac acaccgagag    3720
gacccttcgt cgttcccggg tctctagact cacaggccca tccctctgt aagtgggatc    3780 cgaaaaaaag gtcttcgaa                                                 3799
```

<210> SEQ ID NO 3
<211> LENGTH: 68
<212> TYPE: PRT
<213> ORGANISM: Homo sapien

<400> SEQUENCE: 3

```
Met Ser Gly Ala Asp Arg Ser Pro Asn Ala Gly Ala Ala Pro Asp Ser
 1               5                  10                  15

Ala Pro Gly Gln Ala Ala Val Ala Ser Ala Tyr Gln Arg Phe Glu Pro
            20                  25                  30

Arg Ala Tyr Leu Arg Asn Asn Tyr Ala Pro Pro Arg Gly Asp Leu Cys
        35                  40                  45

Asn Pro Asn Gly Val Gly Pro Trp Lys Leu Arg Cys Leu Ala Gln Thr
    50                  55                  60

Phe Ala Thr Gly
65
```

<210> SEQ ID NO 4
<211> LENGTH: 69
<212> TYPE: PRT
<213> ORGANISM: Homo sapien

<400> SEQUENCE: 4

```
Glu Val Ser Gly Arg Thr Leu Ile Asp Ile Gly Ser Gly Pro Thr Val
 1               5                  10                  15

Tyr Gln Leu Leu Ser Ala Cys Ser His Phe Glu Asp Ile Thr Met Thr
            20                  25                  30

Asp Phe Leu Glu Val Asn Arg Gln Glu Leu Gly Arg Trp Leu Gln Glu
        35                  40                  45

Glu Pro Gly Ala Phe Asn Trp Ser Met Tyr Ser Gln His Ala Cys Leu
    50                  55                  60

Ile Glu Gly Lys Gly
65
```

<210> SEQ ID NO 5
<211> LENGTH: 145
<212> TYPE: PRT
<213> ORGANISM: Homo sapien

<400> SEQUENCE: 5

```
Glu Cys Trp Gln Asp Lys Glu Arg Gln Leu Arg Ala Arg Val Lys Arg
 1               5                  10                  15

Val Leu Pro Ile Asp Val His Gln Pro Gln Pro Leu Gly Ala Gly Ser
            20                  25                  30

Pro Ala Pro Leu Pro Ala Asp Ala Leu Val Ser Ala Phe Cys Leu Glu
        35                  40                  45

Ala Val Ser Pro Asp Leu Ala Ser Phe Gln Arg Ala Leu Asp His Ile
    50                  55                  60
```

```
Thr Thr Leu Leu Arg Pro Gly Gly His Leu Leu Ile Gly Ala Leu
 65                  70                  75                  80

Glu Glu Ser Trp Tyr Leu Ala Gly Glu Ala Arg Leu Thr Val Val Pro
                 85                  90                  95

Val Ser Glu Glu Val Arg Glu Ala Leu Val Arg Ser Gly Tyr Lys
            100                 105                 110

Val Arg Asp Leu Arg Thr Tyr Ile Met Pro Ala His Leu Gln Thr Gly
        115                 120                 125

Val Asp Asp Val Lys Gly Val Phe Phe Ala Trp Ala Gln Lys Val Gly
    130                 135                 140

Leu
145

<210> SEQ ID NO 6
<211> LENGTH: 936
<212> TYPE: DNA
<213> ORGANISM: Homo sapien

<400> SEQUENCE: 6
ggcagcatga gcggcgcaga ccgtagcccc aatgcgggcg cagcccctga ctcggccccg    60
ggccaggcgg cggtggcttc ggcctaccag cgcttcgagc cgcgcgccta cctccgcaac   120
aactacgcgc cccctcgcgg ggacctgtgc aacccgaacg cgtcgggcc gtggaagctg    180 cgctgcttgg cgcagacctt cgccaccggt gaagtgtccg acgcacccct catcgacatt   240
ggttcaggcc ccaccgtgta ccagctgctc agtgcctgca gccactttga ggacatcacc   300
atgacagatt tcctggaggt caaccgccag gagctggggc gctggctgca ggaggagccg   360
ggggccttca actggagcat gtacagccaa catgcctgcc tcattgaggg caaggggaa    420 tgctggcagg ataaggagcg ccagctgcga gccagggtga acgggtcct gcccatcgac    480 gtgcaccagc cccagcccct gggtgctggg agcccagctc ccctgcctgc tgacgccctg   540
gtctctgcct tctgcttgga ggctgtgagc ccagatcttg ccagctttca gcgggccctg   600
gaccacatca ccacgctgct gaggcctggg ggcacctcc tcctcatcgg ggccctggag   660
gagtcgtggt acctggctgg ggaggccagg ctgacggtgg tgccagtgtc tgaggaggag   720
gtgagggagg ccctggtgcg tagtggctac aaggtccggg acctccgcac ctatatcatg   780
cctgcccacc ttcagacagg cgtagatgat gtcaagggcg tcttcttcgc ctgggctcag   840
aaggttgggc tgtgagggct gtacctggtg ccctgtggcc cccacccacc tggattccct   900
gttctttgaa gtggcaccta ataaagaaat aatacc                              936

<210> SEQ ID NO 7
<211> LENGTH: 936
<212> TYPE: DNA
<213> ORGANISM: Homo sapien

<400> SEQUENCE: 7
ccgtcgtact cgccgcgtct ggcatcgggg ttacgcccgc gtcggggact gagccggggc    60
ccggtccgcc gccaccgaag ccggatggtc gcgaagctcg gcgcgcggat ggaggcgttg   120
ttgatgcgcg gggagcgcc cctggacacg ttgggcttgc cgcagcccgg caccttcgac    180
gcgacgaacc gcgtctggaa gcggtggcca cttcacaggc ctgcgtggga gtagctgtaa   240
ccaagtccgg ggtggcacat ggtcgacgag tcacggacgt cggtgaaact cctgtagtgg   300
tactgtctaa aggacctcca gttggcggtc ctcgaccccg cgaccgacgt cctcctcggc   360
```

-continued

```
cccggaagt tgacctcgta catgtcggtt gtacggacgg agtaactccc gttccccctt      420
acgaccgtcc tattcctcgc ggtcgacgct cggtcccact tgcccagga cgggtagctg      480 cacgtggtcg gggtcgggga cccacgaccc tcgggtcgag gggacggacg actgcgggac     540
cagagacgga agacgaacct ccgacactcg ggtctagaac ggtcgaaagt cgcccgggac     600
ctggtgtagt ggtgcgacga ctccggaccc cccgtggagg aggagtagcc ccgggacctc    660
ctcagcacca tggaccgacc cctccggtcc gactgccacc acggtcacag actcctcctc    720
cactccctcc gggaccacgc atcaccgatg ttccaggccc tggaggcgtg gatatagtac    780
ggacgggtgg aagtctgtcc gcatctacta cagttcccgc agaagaagcg gacccgagtc    840
ttccaacccg acactcccga catggaccac gggacaccgg gggtgggtgg acctaaggga   900
caagaaactt caccgtggat tatttcttta ttatgg                              936
```

<210> SEQ ID NO 8
<211> LENGTH: 282
<212> TYPE: PRT
<213> ORGANISM: Homo sapien

<400> SEQUENCE: 8

```
Met Ser Gly Ala Asp Arg Ser Pro Asn Ala Gly Ala Ala Pro Asp Ser
 1               5                  10                  15

Ala Pro Gly Gln Ala Ala Val Ala Ser Ala Tyr Gln Arg Phe Glu Pro
            20                  25                  30

Arg Ala Tyr Leu Arg Asn Asn Tyr Ala Pro Pro Arg Gly Asp Leu Cys
        35                  40                  45

Asn Pro Asn Gly Val Gly Pro Trp Lys Leu Arg Cys Leu Ala Gln Thr
    50                  55                  60

Phe Ala Thr Gly Glu Val Ser Gly Arg Thr Leu Ile Asp Ile Gly Ser
65                  70                  75                  80

Gly Pro Thr Val Tyr Gln Leu Leu Ser Ala Cys Ser His Phe Glu Asp
                85                  90                  95

Ile Thr Met Thr Asp Phe Leu Glu Val Asn Arg Gln Glu Leu Gly Arg
            100                 105                 110

Trp Leu Gln Glu Glu Pro Gly Ala Phe Asn Trp Ser Met Tyr Ser Gln
        115                 120                 125

His Ala Cys Leu Ile Glu Gly Lys Gly Glu Cys Trp Gln Asp Lys Glu
    130                 135                 140

Arg Gln Leu Arg Ala Arg Val Lys Arg Val Leu Pro Ile Asp Val His
145                 150                 155                 160

Gln Pro Gln Pro Leu Gly Ala Gly Ser Pro Ala Pro Leu Pro Ala Asp
                165                 170                 175

Ala Leu Val Ser Ala Phe Cys Leu Glu Ala Val Ser Pro Asp Leu Ala
            180                 185                 190

Ser Phe Gln Arg Ala Leu Asp His Ile Thr Thr Leu Leu Arg Pro Gly
        195                 200                 205

Gly His Leu Leu Leu Ile Gly Ala Leu Glu Glu Ser Trp Tyr Leu Ala
    210                 215                 220

Gly Glu Ala Arg Leu Thr Val Val Pro Val Ser Glu Glu Val Arg
225                 230                 235                 240

Glu Ala Leu Val Arg Ser Gly Tyr Lys Val Arg Asp Leu Arg Thr Tyr
                245                 250                 255

Ile Met Pro Ala His Leu Gln Thr Gly Val Asp Asp Val Lys Gly Val
            260                 265                 270
```

```
Phe Phe Ala Trp Ala Gln Lys Val Gly Leu
    275                 280
```

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
tgtaaaacga cggccagt                                                   18

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
caggaaacag ctatgacc                                                   18

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
tgtaaaacga cggccagtcg aagtggcggg aacaacccga a                         41

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
caggaaacag ctatgaccga cgaggcccca daccccgcca ggct                      44

<210> SEQ ID NO 13
<211> LENGTH: 43
<212> TYPE: DNA
<213> ORGANISM: Artificial Sequence
<220> FEATURE:
<223> OTHER INFORMATION: Primer

<400> SEQUENCE: 13
tgtaaaacga cggccagtga gttgtgtggc agttctaagg gaa                       43

<210> SEQ ID NO 14
<211> LENGTH: 47
<212> TYPE: DNA
<213> ORGANISM: Artificial Sequence
<220> FEATURE:
<223> OTHER INFORMATION: Primer

<400> SEQUENCE: 14
caggaaacag ctatgaccgc tgaccgccga gccgcccggg gccatgt                   47

<210> SEQ ID NO 15
<211> LENGTH: 44
<212> TYPE: DNA

-continued

```
<213> ORGANISM: Artificial Sequence
<220> FEATURE:
<223> OTHER INFORMATION: Primer

<400> SEQUENCE: 15
tgtaaaacga cggccagtac actaagggag atggatgaat gggt                    44

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
caggaaacag ctatgacctc tgccctctc ctaagggatg tt                       42

<210> SEQ ID NO 17
<211> LENGTH: 41
<212> TYPE: DNA
<213> ORGANISM: Artificial Sequence
<220> FEATURE:
<223> OTHER INFORMATION: Primer

<400> SEQUENCE: 17
tgtaaaacga cggccagtag atgcagggga gggaagggta a                       41

<210> SEQ ID NO 18
<211> LENGTH: 47
<212> TYPE: DNA
<213> ORGANISM: Artificial Sequence
<220> FEATURE:
<223> OTHER INFORMATION: Primer

<400> SEQUENCE: 18
tgtaaaacga cggccagtca gaagagaaaa aggagcaaca tccctta                 47

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
caggaaacag ctatgaccgg cgcatgcctg taatcccagc tacta                   45

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
tgtaaaacga cggccagtcc gggttcaagc gattctcttg cctcagctt               49

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
caggaaacag ctatgaccgg cagaggaaga gggtcctggt                         40
```

```
<210> SEQ ID NO 22
<211> LENGTH: 44
<212> TYPE: DNA
<213> ORGANISM: Artificial Sequence
<220> FEATURE:
<223> OTHER INFORMATION: Primer

<400> SEQUENCE: 22
caggaaacag ctatgaccaa agctggcaag atctgggctc acag           44

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
tgtaaaacga cggccagttg gtctctgcct tctgcttgga                40

<210> SEQ ID NO 24
<211> LENGTH: 43
<212> TYPE: DNA
<213> ORGANISM: Artificial Sequence
<220> FEATURE:
<223> OTHER INFORMATION: Primer

<400> SEQUENCE: 24
caggaaacag ctatgaccaa gcctagggtg aatgtctccc cta            43
```